US010463870B2

(12) United States Patent
Roth et al.

(10) Patent No.: US 10,463,870 B2
(45) Date of Patent: Nov. 5, 2019

(54) SYSTEMS AND METHODS FOR CONTROLLING ELECTRIC FIELD PULSE PARAMETERS USING TRANSCRANIAL MAGNETIC STIMULATION

(71) Applicant: YEDA RESEARCH & DEVELOPMENT CO. LTD. AT THE WEIZMANN INSTITUTE OF SCIENCE, Rehovot (IL)

(72) Inventors: Yiftach Roth, D.N. Efrayim (IL); Vadim Chudnovsky, Jerusalem (IL); Noach Safra, Jerusalem (IL); David Hazani, D.N. Efrayim (IL); Abraham Zangen, Jerusalem (IL)

(73) Assignee: Yeda Research & Development Co. Ltd. at the Weizmann Institute of Science, Rehovot (IL)

( * ) Notice: Subject to any disclaimer, the term of this patent is extended or adjusted under 35 U.S.C. 154(b) by 0 days.

(21) Appl. No.: 15/242,737

(22) Filed: Aug. 22, 2016

(65) Prior Publication Data

US 2017/0028212 A1 Feb. 2, 2017

Related U.S. Application Data

(63) Continuation of application No. 13/202,578, filed as application No. PCT/IB2009/055704 on Dec. 11, 2009, now Pat. No. 9,421,393, which is a continuation of application No. 12/332,459, filed on Dec. 11, 2008, now Pat. No. 9,180,305.

(51) Int. Cl.
*A61N 2/00* (2006.01)
*A61N 2/02* (2006.01)

(52) U.S. Cl.
CPC .............. *A61N 2/006* (2013.01); *A61N 2/02* (2013.01)

(58) Field of Classification Search
CPC ............................... A61N 2/004; A61N 2/008
See application file for complete search history.

(56) References Cited

U.S. PATENT DOCUMENTS

| 5,061,234 | A * | 10/1991 | Chaney | A61N 1/40 600/14 |
|---|---|---|---|---|
| 2003/0028072 | A1 * | 2/2003 | Fischell | A61N 1/32 600/13 |
| 2005/0154426 | A1 * | 7/2005 | Boveja | A61N 1/36007 607/45 |
| 2009/0018384 | A1 * | 1/2009 | Boyden | A61N 2/02 600/13 |
| 2010/0298623 | A1 * | 11/2010 | Mishelevich | A61N 2/006 600/13 |

FOREIGN PATENT DOCUMENTS

WO  WO 2006134598 A2 * 12/2006  ............. A61N 2/006

\* cited by examiner

*Primary Examiner* — Christine H Matthews
(74) *Attorney, Agent, or Firm* — Daniel J. Swirsky; Ricki L. Simon; AlphaPatent Associates Ltd.

(57) ABSTRACT

A system and methods for controlling pulse parameters during transcranial magnetic stimulation are provided. Multiple coils are placed on external body parts, and are controlled using an external control unit coupled to a stimulator having fast switches. The timing of the switches, as well as other parameters within the stimulator, determine the pulse parameters, such as pulse shape. The variety of pulse shapes obtainable using such a system and methods provides controlled physiologic effects within an internal body organ.

16 Claims, 26 Drawing Sheets

SYSTEMS AND METHODS FOR CONTROLLING ELECTRIC FIELD PULSE PARAMETERS USING TRANSCRANIAL MAGNETIC STIMULATION

CROSS-REFERENCE TO RELATED APPLICATIONS

This application is a continuation of U.S. patent application Ser. No. 13/202,578, filed Aug. 21, 2011, now U.S. Pat. No. 9,421,393, issued Aug. 23, 2016, which is a U.S. National Phase Application under 35 U.S.C. 371 of PCT International Application No. PCT/IB2009/055704, which has an international filing date of Dec. 11, 2009, and which is a continuation of, and claims the benefit of priority from, U.S. patent application Ser. No. 12/332,459, filed Dec. 11, 2008, now U.S. Pat. No. 9,180,305, issued Nov. 10, 2015, the disclosures of which are incorporated herein by reference in their entirety.

FIELD OF THE INVENTION

The present invention relates to systems and methods for controlling and varying electric field pulse parameters produced in a body organ through the use of transcranial magnetic stimulation, thus affecting properties of resulting neuronal activation in the organ.

BACKGROUND OF THE INVENTION

Transcranial magnetic stimulation (TMS) is a noninvasive technique used to apply brief magnetic pulses to the brain, or to other human organs, and to thereby activate neuronal structures. The pulses are administered by passing high currents by a stimulator through an electromagnetic coil externally placed upon the patient (for example, placed on the scalp for brain treatment), inducing electrical currents in the underlying tissue, thereby producing a localized axonal depolarization. This technique has become a major tool in central nervous system research, as well as a potentially promising treatment option for various neurobehavioral and neurological disorders.

In most TMS devices, a capacitor is charged to a predefined voltage, and the magnetic stimulation is performed by discharging the capacitor through a single stimulating coil, using a single fast switch. The brief current in the TMS coil induces an electric field proportional to the time derivative of the current. When applied to neuronal tissue, the electric field may lead to a change in the neuronal transmembrane potential. This potential change may result in either hyper-polarization or depolarization of the membrane. When the membrane is depolarized to a critical level, then under certain conditions a neuronal stimulation will occur.

The current pulse shape produced in conventional TMS devices is either monophasic or biphasic sinusoidal. The pulse shape is determined by the capacitance of the capacitor C, the stimulating coil inductance L, and the resistance R in the circuit. In stimulators with biphasic pulses unlike with monophasic pulses part of the energy returns to the capacitor at the end of a cycle, enabling repetitive operation. Hence, biphasic pulses are used in repetitive TMS (rTMS), while monophasic pulses are usually used to produce single pulses.

A method termed controllable TMS (cTMS) has been disclosed in Peterchev et al.: A Transcranial Magnetic Stimulator Inducing Near-Rectangular Pulses With Controllable Pulse Width (cTMS), IEEE Trans Biomed Eng 2008, 55:257-266. In this method, an insulated gate bipolar transistor (IGBT) is used as a switch, and a monophasic pulse can be truncated in a controlled way by turning off the IGBT. Energy from the coil is dissipated in a resistor and is not returned to the capacitor; hence the ability for repetitive TMS in this method is limited. The extension of this method to a biphasic pulse shape is disclosed in US Patent Publication Number 2007/0293916 A1. This is done by using two capacitors and IGBTs for the two phases. However, in this method the switching is usually performed while the current is high, which may lead to serious problems of transient voltage spikes and switching losses. Moreover, this disclosure is limited to producing rectangular pulse shapes only. In addition, in this disclosure there is no possibility of inducing different pulse shapes in different body organs or body organ regions. Moreover, only the use of a single coil is disclosed.

The exact neuronal tissue response may depend on the specific pulse parameters, such as pulse shape, of the induced electric field. Thus, it would be advantageous to have a method to induce variations in pulse parameters, such as pulse shape, in a controlled way. Increased variability and flexibility in control of pulse shape parameters may be useful for brain research as well as for various clinical applications in psychiatry, neurology and disorders related to peripheral nerves.

A method of multi-channel transcranial magnetic stimulation was disclosed in US Patent Publication Number US20060287566. In this method, different coil elements are operated using separate channels. The multiple channels may be activated simultaneously, or sequentially with different delay times. The time delays between the operation of each channel are controlled on a level of microseconds. This disclosure does not refer to specific control of pulse parameters, pulse shape and pulse polarity as in the present invention.

SUMMARY OF THE INVENTION

There is provided, in accordance with one embodiment of the present invention, a system for transcranial magnetic stimulation. The system includes a first electromagnetic stimulating coil configured to be placed on a first external body part of a body, a second electromagnetic stimulating coil configured to be placed at a second location, a stimulator for providing a high current to an electromagnetic coil, the stimulator electrically coupled to the first and second electromagnetic stimulating coils. The stimulator includes at least one energy storage device configured to discharge current into at least one of the electromagnetic stimulating coils, thus resulting in an electric field pulse in an internal body organ and at least one externally-controllable fast switch coupled to at least one energy storage device and to at least one electromagnetic stimulating coil, for control of parameters of the discharged current pulse. The system further includes an external control unit in electrical communication with the stimulator for controlling parameters of the externally-controllable fast switch thus providing control of at least one parameter of the current pulse, thereby inducing a controlled physiologic effect in a neuronal structure.

There is provided, in accordance with another embodiment of the present invention, a method for producing a physiological effect in an internal body organ using transcranial magnetic stimulation. The method includes providing a system having a first and a second electromagnetic stimulating coil, a stimulator for stimulating the first and second electromagnetic stimulating coils, the stimulator including at least one energy storage device and at least one externally-controllable fast switch, and an external control unit in electrical communication with the stimulator for controlling the fast switch, positioning the first electromagnetic stimulating coil on a first body part, positioning the second electromagnetic stimulating coil at a second location, controlling a parameter of the at least one externally-controllable fast switch using the external control unit, thus providing a controlled current pulse, and discharging the controlled current pulse through at least one of the first and second electromagnetic stimulating coils, thereby producing an electric field pulse at an internal body part.

The energy storage device may include multiple energy storage devices and the externally-controllable fast switch may include multiple fast switches coupled to one or multiple energy storage devices. The external control unit is configured to provide control of timing of turning on or off of said at least one externally-controllable fast switch, an amplitude of initial voltage on the energy storage device, a frequency of discharging of the energy storage device, a time interval between pulses or combinations of pulses, a pulse width of each pulse, relative polarities of current directions in the electromagnetic stimulating coils at each period of operation, direction of current flow in the electromagnetic stimulating coils at each period of operation, and numbers of each type of pulse.

The second location for placement of the second electromagnetic stimulating coil may be remote from the body. Alternatively, the second location may be a second external body part wherein the first and second external body parts may be the same body part, different regions of the same body part, or different body parts. The internal body organ may be a neuronal tissue in the brain, spinal cord or in a peripheral nerve, wherein the controlled electric field pulse is configured to have a physiological effect on a neuronal structure. The physiological effect may be related to a threshold for neuronal activation, an amplitude of an induced neuronal action potential, a latency of an induced neuronal action potential, depolarization of a neuronal membrane, hyperpolarization of a neuronal membrane, a rate of depolarization or hyperpolarization or any other parameter.

The first and second electromagnetic stimulating coils may have the same inductance or different inductances. They may be connected in series or parallel. The system may include multiple coils having the same or different inductances as other coils and being connected in any combination of series and parallel. The fast switch may be turned on or off when current flowing through the system is low, thereby reducing voltage spikes and switching losses, or when current flowing through the system is high, which may require special components. The first and second electromagnetic stimulating coils may be coupled to one energy storage device for both of them, a first energy storage device for the first electromagnetic stimulating coil and a second energy storage device for the second electromagnetic stimulating coil, or a first energy storage device during a first period of operation and a second energy storage device during a second period of operation or any other combination thereof. At least one of the coils may be configured to have reduced heating and reduced energy consumption. Reduced energy consumption may allow for the stimulator to provide the current at high frequencies. The stimulator may also be configured to provide reduced voltage or electric currents, thereby enabling use of components having a reduced size and/or price. In some embodiments, the first electromagnetic stimulating coil is connected to a first channel and the second electromagnetic stimulating coil is connected to a second channel.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1:
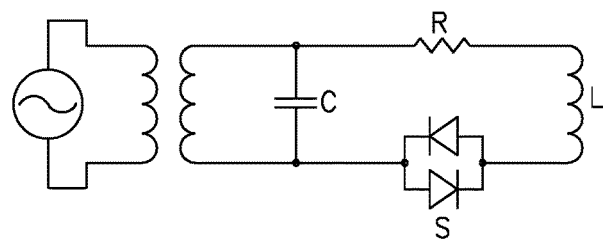
FIG. 1 is a schematic illustration of a conventional TMS device.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to systems and methods for controlling pulse parameters using transcranial magnetic stimulation (TMS). The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

In conventional TMS devices, an electrical energy storage device, such as a capacitor, is discharged through a single stimulating coil using a fast switch. A schematic illustration of a conventional TMS device is shown in FIG. 1. A capacitor C is charged to a pre-defined voltage, and upon operation it is discharged through a single stimulating coil L, producing a current pulse within coil L. A high current fast switch S is used to control current flow. The resistance in the circuit is depicted as R. When the coil is placed over a body organ, such as the head, it may produce an electric field pulse in the tissue, which is proportional to the time derivative of the current pulse in the coil. The electric field pulse in the tissue may induce a change in the trans-membrane potential in neuronal structures. When the neuronal membrane is depolarized to a threshold level, neuronal activation may occur.

Figure 2A:
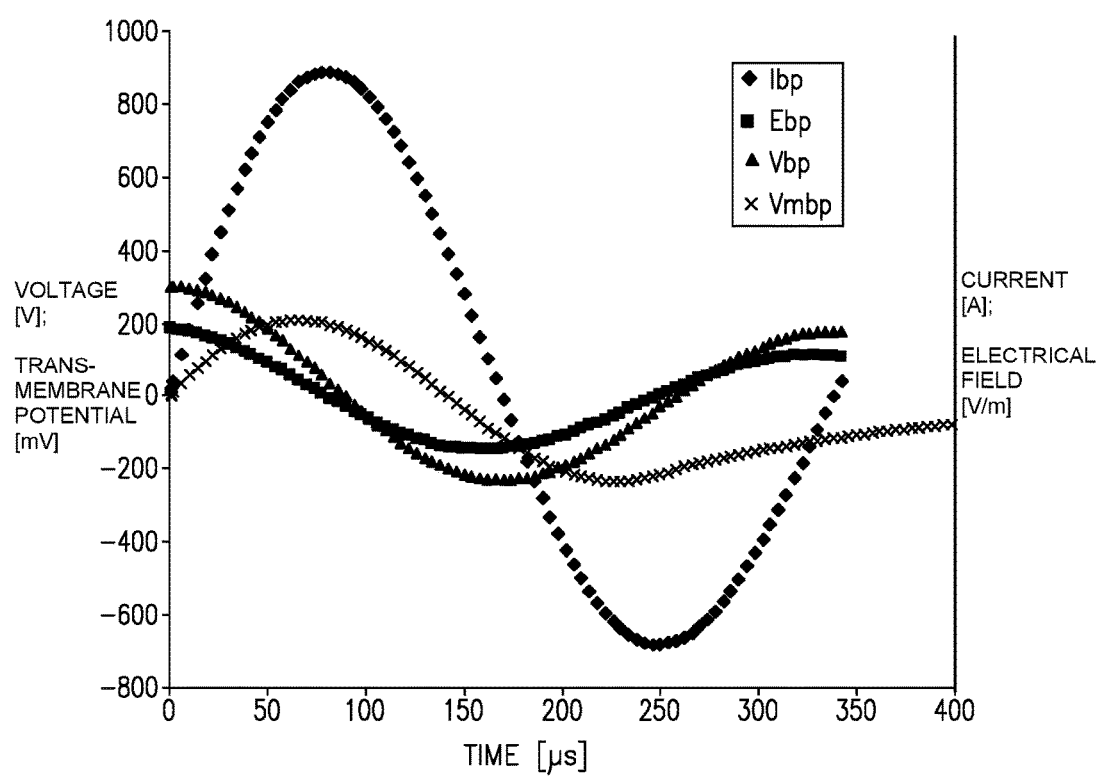
FIG. 2A is a graphical illustration of an example of a biphasic pulse produced by a TMS device.

Conventional TMS devices produce either a biphasic or a monophasic pulse shape. An example of a biphasic pulse is shown in FIG. 2A. Shown are the coil current Ibp (diamonds), the electric field Ebp (squares), the voltage in the capacitor Vbp (triangles), and the change in the trans-membrane potential which may occur in a neuronal structure, Vmbp (x's). The parameters used in the example are capacitance $C=180$ μF, inductance $L=16$ μH, resistance $R=0.05$ Ohm, and initial voltage in the capacitor $V_0=300$ V. The units of Ibp are ampere, of Vbp are V, of Ebp are V/meter, and Vmbp which is usually measured in mV—is shown in FIG. 2A in normalized units to fit the graph scale.

It can be seen from FIG. 2A that part of the electrical energy returns to the capacitor at the end of a cycle, hence Vbp at the end of a cycle has a value which is a considerable fraction of the initial value $V_0$. Hence stimulators producing biphasic pulses can in general be used for repetitive TMS (rTMS).

Figure 2B:
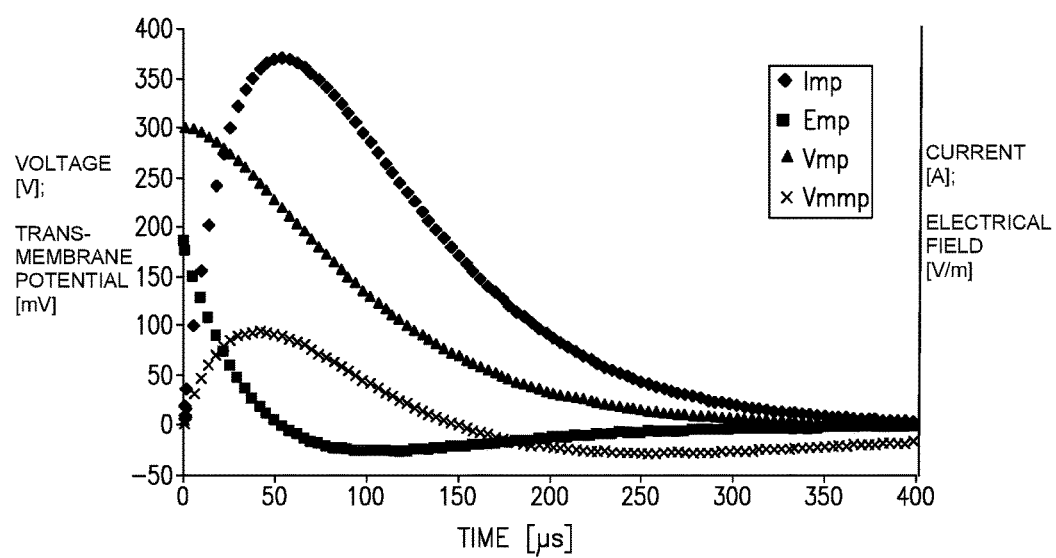
FIG. 2B is a graphical illustration of a monophasic pulse produced by a TMS device.

An example of a monophasic pulse is shown in FIG. 2B. Shown are the coil current Imp (diamonds), the electric field Emp (squares), the voltage in the capacitor Vmp (triangles), and the change in the trans-membrane potential which may occur in a neuronal structure, Vmbp (x's). The parameters used in the example are the same as in FIG. 2A, except the resistance which is $R=\sqrt{(4L/C)}=0.596$ Ohm, in order to make the circuit critically damped. The units are the same as in FIG. 2A. It should be noted, however, that the units are exemplary and should not be regarded as limiting.

It can be seen from FIG. 2B that in contrast to a biphasic pulse, in a monophasic pulse the electrical energy is not returned to the capacitor. Hence the ability to produce monophasic pulses in high frequency repetitive TMS is limited.

The present application discloses systems and methods, which, unlike previous TMS systems and methods, enable production of a variety of pulse shapes for the coil current and for the resulting electric fields which may be obtained in a controllable manner. By providing the ability to produce various pulse shapes, the physiologic effects of TMS can be controlled as well since the physiologic effect produced in a biological tissue may strongly depend on the parameters of the induced electric field pulse. In particular, the threshold for neuronal activation in neuronal tissue may depend on the electric field pulse shape. For instance, the production of an action potential depends on opening of sodium channels in the neuronal membrane. It is well known that there are sodium channels which have three m gates, which are opened upon membrane depolarization and closed upon hyper-polarization, with short time constants, and have one h gate, which is opened upon membrane hyper-polarization and closed upon depolarization, with a long time constant. Hence, it is possible to reduce the threshold for neuronal activation, by inducing a hyper-polarizing pulse just prior to a depolarizing pulse. In contrast, it is possible to increase the threshold for neuronal activation, by inducing a sub-threshold depolarizing pulse prior to a supra-threshold depolarizing pulse. Such manipulation can be used to increase focality of TMS effects, even at deeper brain sites. In addition, the threshold for action potential may also depend on the rate of depolarization [Azouz R, Gray C M. (2000) *Dynamic spike threshold reveals a mechanism for synaptic coincidence detection in cortical neurons in vivo*. Proc Natl Acad Sci USA 97:8110-5; Naundorf B, Wolf F, Volgushev M (2006) *Unique features of action potential initiation in cortical neurons*. Nature 440:1060-1063]. Thus, control of the rate of depolarization could allow for further localization of stimulation effects, particularly when different brain regions are affected with different pulse shapes and/or different rates of depolarization.

In addition to the threshold for neuronal activation, the amplitude of the invoked action potential may also depend on various parameters, including the intensity, rise time, pulse width and pulse shape of depolarizing and/or hyper-polarizing electric field pulses, numbers of depolarizing and/or hyper-polarizing electric field pulses, time intervals between pulses, and frequencies of operation.

Another parameter that may affect the neuronal response is the time delay between pulses. For instance it is known in paired-pulse I-wave rTMS that pulses at I-wave periodicity (1.5 ms and multiples thereof) lead to a facilitatory interaction between the second pulse and the I-waves generated by the first pulse [Ziemann U, Tergau F, Wassermann E M, Wischer S, Hildebrandt J, Paulus W. Demonstration of facilitatory I wave interaction in the human motor cortex by paired transcranial magnetic stimulation. J Physiol (Lond) 1998; 511:181-190; Thickbroom G W, Byrnes M L, Edwards D J, Mastaglia F L. Repetitive paired-pulse TMS at I-wave periodicity markedly increases corticospinal excitability: a new technique for modulating synaptic plasticity. Clin Neurophysiol 2006; 117:61-66]. In contrast, other inter-stimulus intervals (ISI), such as 1 ms or 2.5 ms, may lead to inhibition [Roshan L, Paradiso G O, Chen R. Two phases of short-interval intracortical inhibition. Exp Brain Res 2003; 151:330-337]. The systems of the present invention may be used to induce two or more TMS pulses, over different brain regions, with different Ns. The amplitude of each pulse may be controlled, addition, the amplitude of the effect induced in each brain region by a certain pulse may depend on the position and orientation of the coil or coil element which produces the pulse. This way the systems and method disclosed here may enable facilitation in certain brain regions, and/or inhibition in other brain regions. The inter-stimulus interval between each set of pulses could be adjusted to match each individual's wave pattern. Thus, for instance I-wave periodicity could be done with intervals adjusted according to the individual's I-wave peaks, rather than with 1.5 ms intervals. This method may enable increased focality of the TMS effect in certain brain regions, including deep brain regions. In addition, the ability to induce facilitation in certain brain regions, and inhibition in other brain regions, may improve the clinical outcome in various neurological and psychiatric disorders, including depression, bi-polar disorder, addiction, eating disorder, obesity, stroke rehabilitation, epilepsy, migraine, Parkinson's disease, schizophrenia, autism, post-traumatic stress disorder, Tourett's syndrome, blepharospasm, and more.

The systems and methods of the present invention advantageously include multiple electromagnetic stimulating coils, with similar and/or different inductances, electrically connected either in parallel, or in series, or both in parallel and in series, with one or more energy storage devices, which are coupled to the coils using one or more fast switches, where the timing of turning on and/or turning off of each switch is controllable by the user. In some embodiments, the switches may be turned on and/or off when the current is small, reducing voltage spikes and switching losses. In other embodiments, some or all of the opening and/or closing times of switches may be performed while the current is high. In such cases careful component selection may be required, and may include the use of snubber circuits. In some embodiments, one of the stimulating coils may be attached to a body organ, such as the head, while the other coil/coils are remote from a body organ. In other embodiments, two or more coils are located close to a body organ in the same locations. In yet other embodiments, one or more coils are located close to a body organ at a certain location, while one or more other coils are located close to another body organ, or close to the body organ at different location, such as different locations near a head. This way it may be possible to discriminate between the physiologic effects produced in different regions in the body, such as different brain regions, and/or spinal cord or peripheral nerves regions. For example it may be possible to increase the specificity of the effect induced in a certain brain region, such as in deeper neuronal structures.

The use of two or more coils may also provide savings in power consumption and reduction in coil heating. In particular, one can reduce the amount of current flowing through a coil or coils which are close to a body organ, thus minimizing heating problems.

The use of two or more coils may also enable reduction of voltages required to induce neuronal activation. Moreover, it may also enable reduction of the required electric currents induced in the stimulating coils. Thus, by using multiple coils in the systems and methods of the present application, it may be possible to use cheaper and/or smaller components in the system than in current TMS stimulators, since the system may be designed to withstand smaller values of voltages and/or currents.

The capacitor energy is proportional to $\frac{1}{2}CV^2$, where C is the capacitance and V is the voltage. Hence, the ability to restore part of the voltage to the capacitor or capacitors at the end of a cycle with a certain pulse shape may enable repetitive operation at higher frequencies, using various pulse shapes apart from biphasic, including monophasic pulses or any other pulse shape as disclosed in this application.

Figure 3:
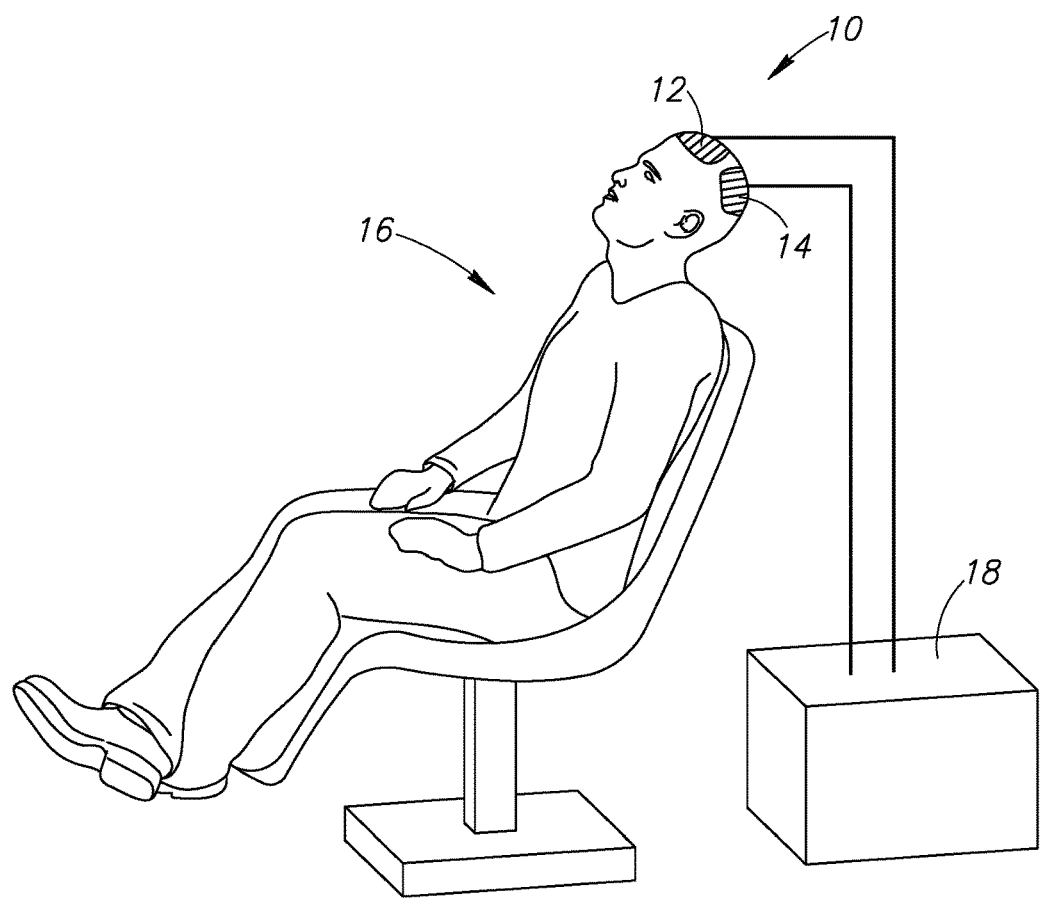
FIG. 3 is a schematic illustration of a system in accordance with an embodiment of the present invention.

Reference is now made to FIG. 3, which is a schematic illustration of a system 10 in accordance with an embodiment of the present invention. System 10 includes a first electromagnetic stimulating coil 12 and a second electromagnetic stimulating coil 14, each of which is positionable on a body of a subject 16. In the embodiment shown herein, first and second electromagnetic stimulating coils 12 and 14 are positioned on a head of subject 16 for use in treating the brain. It should be readily apparent, however, that other body parts may be used with system 10 as well. A stimulator 18 is electrically coupled to the first and second electromagnetic stimulating coils 12 and 14, and is configured to provide a high current to the electromagnetic stimulating coils. In some embodiments, separate stimulators 18 are used for each of first and second electromagnetic stimulating coils 12 and 14.

In some embodiments, first electromagnetic stimulating coil 12 is placed on an external body part, while second electromagnetic stimulating coil 14 is placed remote from the body of the subject. In some embodiments, second electromagnetic stimulating coil 14 is placed on an external body part as well, which may be the same body part, a different region of the same body part, or a different body part.

Producing high currents in first and second electromagnetic stimulating coils 12 and 14 causes an electric field pulse to be produced in an internal body organ. In some embodiments, the internal body organ is a brain, a spinal cord, or a peripheral nerve. In these cases, the electric field pulse may have a physiological effect on a neuronal structure in the internal body organ. For example, the electric field pulse may affect the threshold for neuronal activation, an amplitude of an induced neuronal action potential, a latency of an induced neuronal action potential, depolarization of a neuronal membrane, hyperpolarization of a neuronal membrane, a rate of depolarization or hyperpolarization, facilitation, inhibition, or other parameters.

Figure 4:
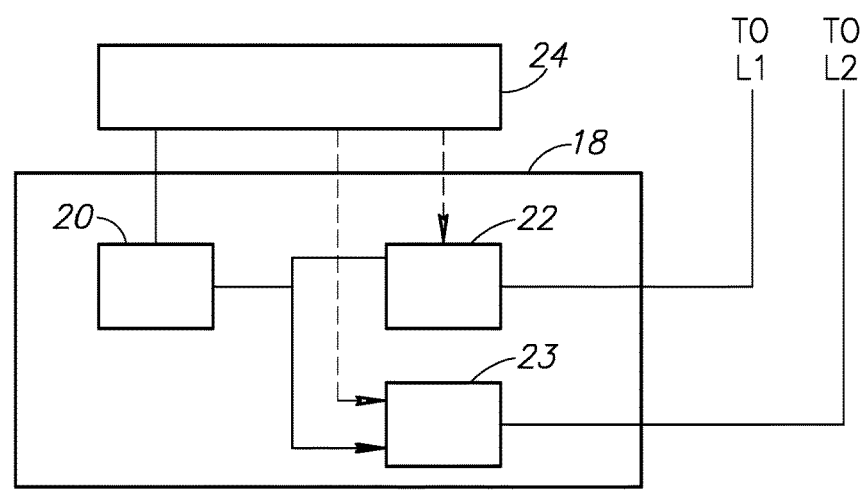
FIG. 4 is a block diagram schematic illustration of a stimulator of the system of FIG. 3, in accordance with embodiments of the present invention.

Reference is now made to FIG. 4, which is a block diagram schematic illustration of stimulator 18, in accordance with embodiments of the present invention. Stimulator 18 includes at least one energy storage device 20 for discharge of current into at least one of the first or second electromagnetic stimulating coils 12 and 14, and at least two externally-controllable fast switches 22 and 23, each one coupled to energy storage device 20 and to at least one of first and second electromagnetic stimulating coils 12 and 14. An external control unit 24 is in electrical communication with stimulator 18 for controlling parameters of energy storage device 20 and fast switches 22 and 23. External control unit 24 allows for turning on/off of fast switches 22 and 23 or of more than two fast switches. External control unit 24 further allows for control of the timing of each turning on/off, amplitude of the initial voltage on the energy storage device 20, frequency of discharging of current of energy storage device 20, time intervals between pulses or combinations of pulses, pulse widths, pulse shapes, duration of pulse trains or pulses or pulse combinations, time intervals between pulse trains, relative polarities of current directions in coils 12 and 14 at different periods of operation, direction of current flow in coils 12 and 14, numbers of each type of pulse, and any other parameters.

In one embodiment of the present invention, first and second electromagnetic stimulating coils 12 and 14 are coupled to one energy storage device. In another embodiment of the present invention, first electromagnetic stimulating coil 12 is coupled to a first energy storage device and second electromagnetic stimulating coil 14 is coupled to a second energy storage device. In yet another embodiment, different periods of operation may require different configurations for example, a first energy storage device may be used during a first period of operation and a second energy storage device may be used during a second period of operation.

It should be readily apparent that multiple energy storage devices 20 and multiple fast switches 22 may be used to control first and second stimulating electromagnetic coil 12 and 14, either in series or in parallel. Moreover, each fast switch 22 or 23 may enable current flow in one or the other direction, and/or in both directions, and the turning on/off of the flow in each direction as well as timing of turning on/off of flow may be controllable separately. Control of time intervals between pulses may include, for example, but not limited to, a range of 0 to 1000 microseconds, a range of 1 to 1000 milliseconds, approximately 1.5 milliseconds or a multiple thereof, approximately 1 millisecond, approximately 2.5 milliseconds, a range of 0.5 to 10 milliseconds, a range of 0.1 to 100 milliseconds, a range of 1 to 500 microseconds, or other ranges. In addition, time intervals between pulses may be adjusted according to an individual's wave pattern, such as I-wave or D-wave peaks. Intervals between pulses in a pulse train may also be variable from one another. The discharged current pulse may be a repetitive monophasic current pulse, a repetitive biphasic current pulse, a repetitive monophasic current pulse with alternating directions, or other configurations. Moreover, more than two electromagnetic stimulating coils may be used in the present invention. Some non-limiting embodiments and examples are presented hereinbelow.

Figure 5:
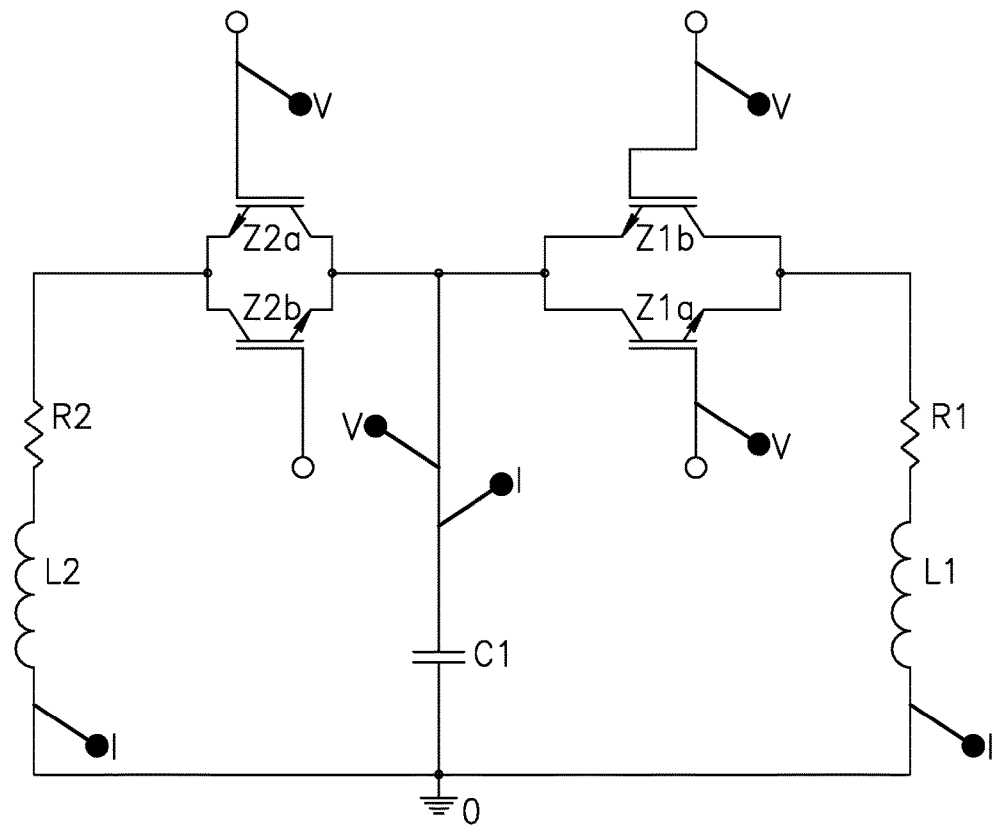
FIG. 5 is a circuit diagram in accordance with one embodiment of the present invention.

Reference is now made to FIG. 5, which is a circuit diagram in accordance with one embodiment of the present invention. In the embodiment shown in FIG. 5, two stimulating coils L1 and L2 are connected in parallel, with one capacitor C1 and four switches: Z1a, Z1b, Z2a and Z2b. In the embodiment shown in FIG. 5, switches Z1a, Z1b, Z2a and Z2b are IGBTs; however, any suitable switches may be used. The timing of opening or closing of each switch are controllable by the user.

In certain operations of the circuit shown in FIG. 5 the switching may be performed while the current is close to zero, thus minimizing transient voltage spikes and switching losses. In yet other operations of the circuit the switching may be performed while the current is high. In such cases the use of appropriate snubber circuits may be required, as well as careful selection of components which may withstand spikes of high voltage and/or current. The circuit shown in FIG. 5 can be used with different values of coil inductances, capacitance, resistance in each circuit, initial voltage, and different timings of the opening and closing of each switch. In some embodiments, coils L1 and L2 may be connected to different energy storage devices or capacitors, thus enabling separate control of the initial voltages and hence the current amplitudes in the two coils.

Several examples using the circuit of FIG. 5 are now described.

Example 1

In one non-limiting example, capacitor C1 has capacitance C=25 μF, coil L1 has an inductance of 150 μH, coil L2 has an inductance of 16 μH, the resistances R1 and R2 in the two circuits are both 0.05 Ohm, and two of the switches (Z1a and Z2b) are always closed. The timing of opening or closing of each switch is controllable by the user.

Figure 6:
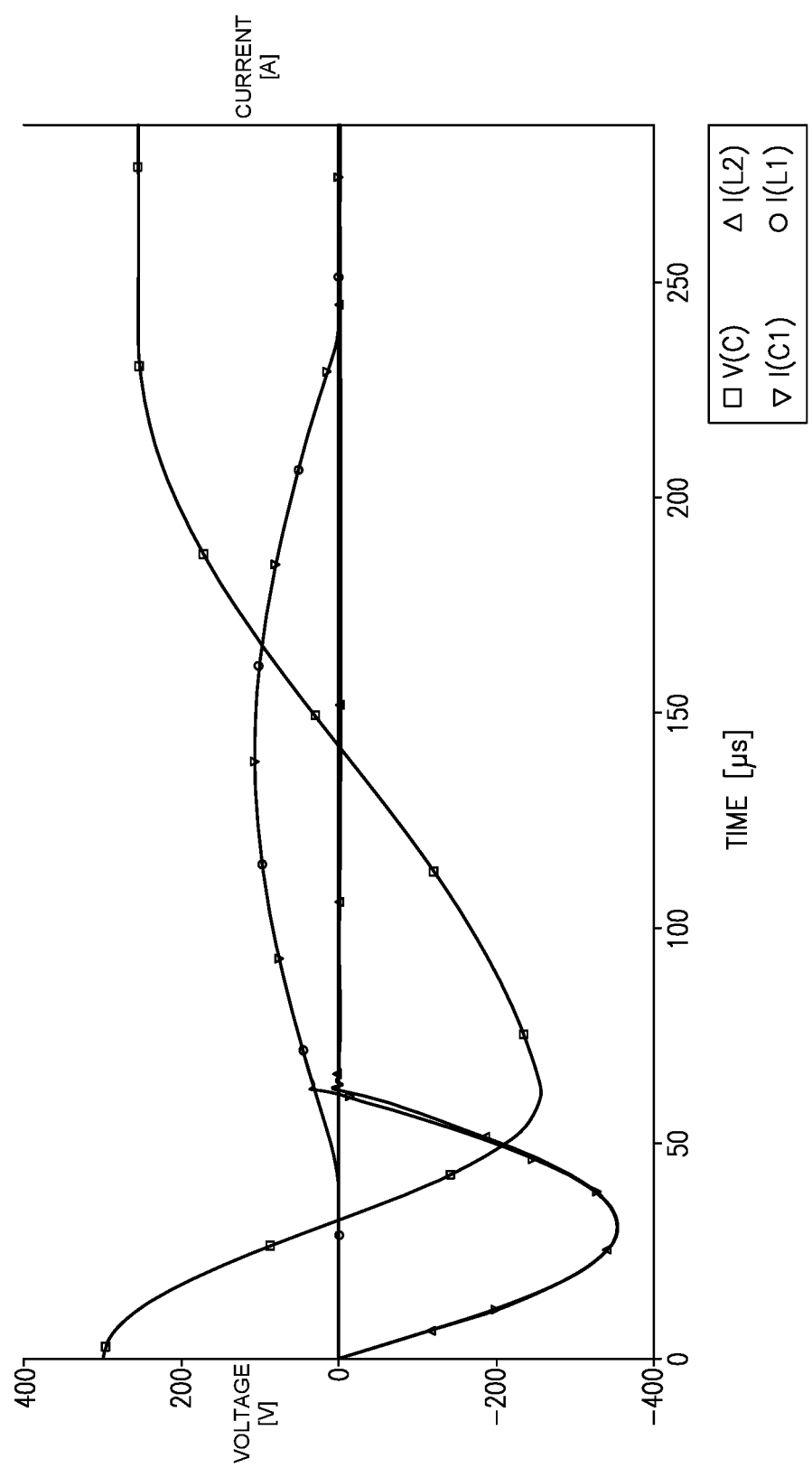
FIG. 6 is a graphical illustration showing pulse shapes which may be produced upon operation of the circuit shown in FIG. 5 in accordance with the parameters of one embodiment of the present invention.

Reference is now made to FIG. 6, which is a graphical illustration showing pulse shapes which may be produced upon operation of the circuit shown in FIG. 5 in accordance with the parameters of Example 1. Depicted in FIG. 6 are the current in L1 I(L1), the current in L2 I(L2), the current near the capacitor I(C1), and the capacitor voltage V(C1). In this example the capacitor is charged to an initial voltage of 300 V. Between 0 and 40 µs only Z2a is opened, allowing current flow only through coil L2. At 40 µs switch Z1b is also opened, allowing current flow through coil L1 (having the larger inductance), in a direction which is opposite to the current flowing through coil L2 (having the smaller inductance). It can be seen that in this example a monophasic pulse is produced in coil L2, and another monophasic pulse is produced in coil L1. However, capacitor voltage V(C1) regains about 85% of its initial value at the end of one cycle. Hence, most of the electric energy is returned to the capacitor, making it feasible to produce high frequency rTMS.

The activation with this circuit may be implemented in several ways. For example:

1. Coil L2 is close to a body organ, such as the head, while coil L1 is remote from the body organ. In this case, a monophasic pulse is induced in the body organ, with the shape of I(L2). This pulse shape may be induced either in a single pulse mode, low frequency or high frequency TMS.

2. Coil L1 is close to a body organ, such as the head, while coil L2 is remote from the body organ. In this case, a monophasic pulse is induced in the body organ, with the shape of I(L1), which has longer pulse width and smaller current amplitude. This pulse shape may be induced either in a single pulse mode, low frequency or high frequency TMS.

3. Both coil L2 and coil L1 are close to a body organ, such as the head, at a close location, with the same current polarity. In this case, a biphasic pulse is induced in the body organ, with a shape similar to I(C1), which is the summation of the pulse shapes of I(L1) and I(L2). The exact pulse shape may be altered due to the magnetic coupling between the coils, and will depend on the coils' configurations and relative orientations, positions and current polarity. This pulse shape may be induced in a single pulse mode, or low frequency or high frequency TMS.

4. Both coil L2 and coil L1 are close to a body organ, such as the head, at a close location, with an opposite current polarity. In this case, a summation of two monophasic pulses is induced in the body organ, which is the summation of the pulse shapes of I(L1) and I(L2), with the same current direction. The exact pulse shape may be altered due to the magnetic coupling between the coils, and will depend on the coils' configurations and relative orientations, positions and current polarity. This pulse shape may be induced either in a single pulse mode, low frequency or high frequency TMS.

5. Same as in 3 or 4, but the two coils are placed close to different body organs, or different locations near a body organ, such as the head. In this case different pulse shapes will be produced at different regions in the body, corresponding to different convolutions of the current pulses induced in the two currents. The exact pulse shape in each region in the body will depend on the distance from each coil, and the amplitudes and temporal features of the current pulses in each coil.

Example 2

In another non-limiting example, capacitor C1 has C=25 uF, coil L1 has an inductance of 16 µH, coil L2 has an inductance of 16 uH (thus, the inductances in the two coils are similar or identical), the resistances R1 and R2 in the two circuits are both 0.05 Ohm, and two of the switches (Z1a and Z2b) are always closed. The timing of opening or closing of each switch is controllable by the user.

Figure 7:
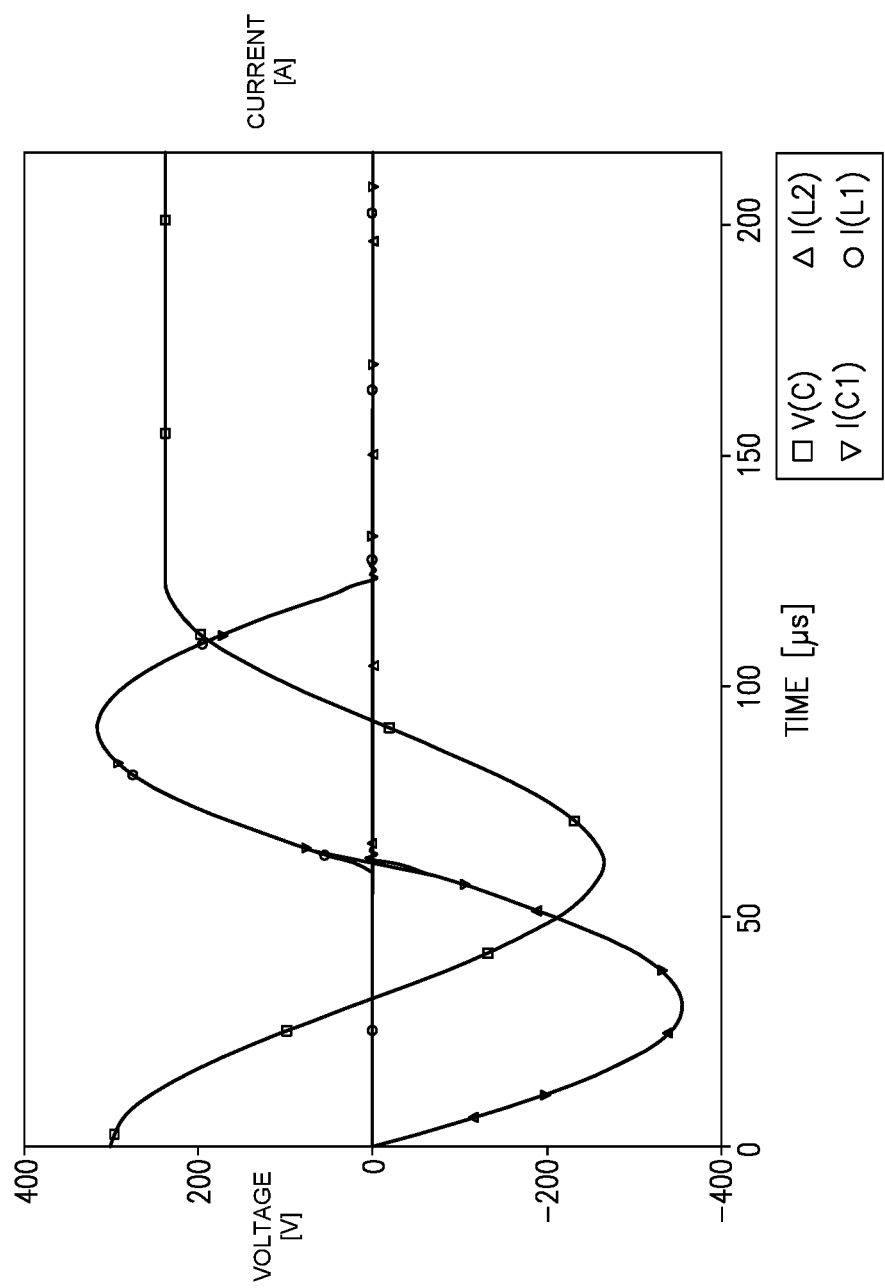
FIG. 7 is a graphical illustration showing pulse shapes which may be produced upon operation of the circuit shown in FIG. 5 in accordance with the parameters of another embodiment of the present invention.

Reference is now made to FIG. 7, which is a graphical illustration showing pulse shapes which may be produced upon operation of the circuit shown in FIG. 5 in accordance with the parameters of Example 2. Depicted in FIG. 7 are the current in L1 I(L1), the current in L2 I(L2), the current near the capacitor I(C1), and the capacitor voltage V(C1). In this example the capacitor is charged to an initial voltage of 300 V. Between 0 and 40 µs only Z2a is opened, allowing current flow only through coil L2. At 40 µs switch Z1b is also opened, allowing current flow through coil L1, in a direction which is opposite to the current flowing through coil L2. It can be seen that in this example a monophasic pulse is produced in coil L2, and another monophasic pulse is produced in coil L1. In this case the combination of the current pulses of the two coils produces a biphasic pulse shape. Yet, the amplitude of the $2^{nd}$ pulse (I(L1) in FIG. 7) relative to the $1^{st}$ pulse (I(L2) in FIG. 7) is higher than in a conventional biphasic pulse induced in a single coil.

It can be seen from FIG. 7 that the capacitor voltage V(C1) regains about 80% of its initial value at the end of one cycle. Hence, it may be feasible to produce high frequency rTMS. The exact value of the capacitor voltage at the end of a cycle may depend on the capacitance, inductances, resistances and temporal features of operation in the system. Activation of this circuit may be done using any of the options described above with reference to FIG. 6.

Example 3

In another non-limiting example, the parameters for capacitor C1, coils L1 and L2, and resistances R1 and R2 are the same as in Example 2. That is, capacitor C1 has C=25 uF, coil L1 has an inductance of 16 µH, coil L2 has an inductance of 16 uH (thus, the inductances in the two coils are similar or identical), the resistances R1 and R2 in the two circuits are both 0.05 Ohm. However, the timing of opening or closing of each switch is changed.

Figure 8:
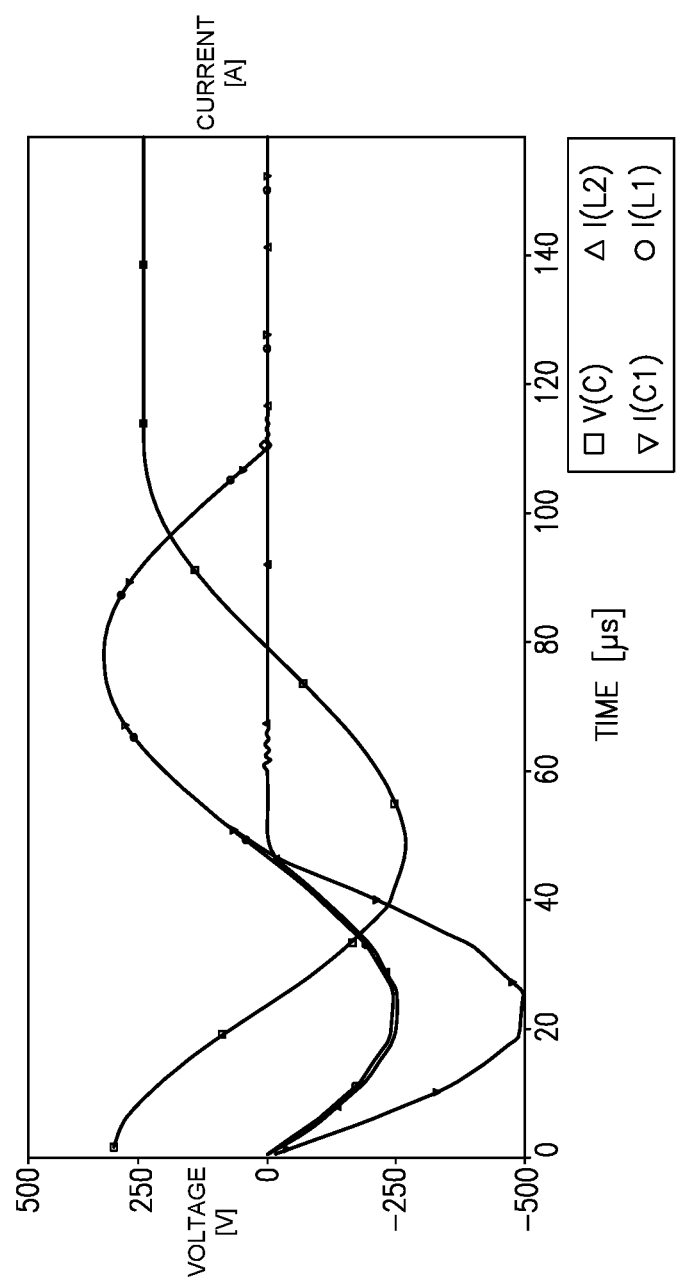
FIG. 8 is a graphical illustration showing pulse shapes which may be produced upon operation of the circuit shown in FIG. 5 in accordance with the parameters of another embodiment of the present invention.

Reference is now made to FIG. 8, which is a graphical illustration showing pulse shapes which may be produced upon operation of the circuit shown in FIG. 5 in accordance with the parameters of Example 3. Depicted in FIG. 8 are the current in L1 I(L1), the current in L2 I(L2), the current near the capacitor I(C1), and the capacitor voltage V(C1). In this example the capacitor is charged to an initial voltage of 300 V. Switches Z1a and Z1b are open between 0 and 110 µs, switch Z2a is open between 0 and 60 µs, and Z2b is always closed. It can be seen that in this example a biphasic pulse is produced in coil L1 between 0 and 110 µs, and a monophasic pulse is produced in coil L2, between 0 and 50 µs. The capacitor voltage V(C1) regains about 80% of its initial value, enabling high frequency repetitive operation. The exact value of the capacitor voltage at the end of a cycle may depend on the capacitance, inductances, resistances and temporal features of operation in the system.

Again, all the options stated for the example in FIG. 6 may be implemented for the example in FIG. 8. In particular, one may induce in a body organ a pulse shape such as I(L1), I(L2) or I(C1), by combining the effects of the two coils (FIG. 8). Note that in this case, in I(C1) a biphasic pulse is produced, with an amplitude of the $1^{st}$ phase relative to the $2^{nd}$ pulse which is higher than in conventional biphasic pulse induced in a single coil.

Example 4

In another non-limiting example, capacitor C1 has C=25 µF, coil L1 has an inductance of 1 µH, coil L2 has an inductance of 16 µH, the resistances in the two circuits are R1=R2=0.05 Ohm, and the initial capacitor voltage is V(C1)=300 V. The timing of opening/closing of each switch is controlled by the user.

Figure 9:
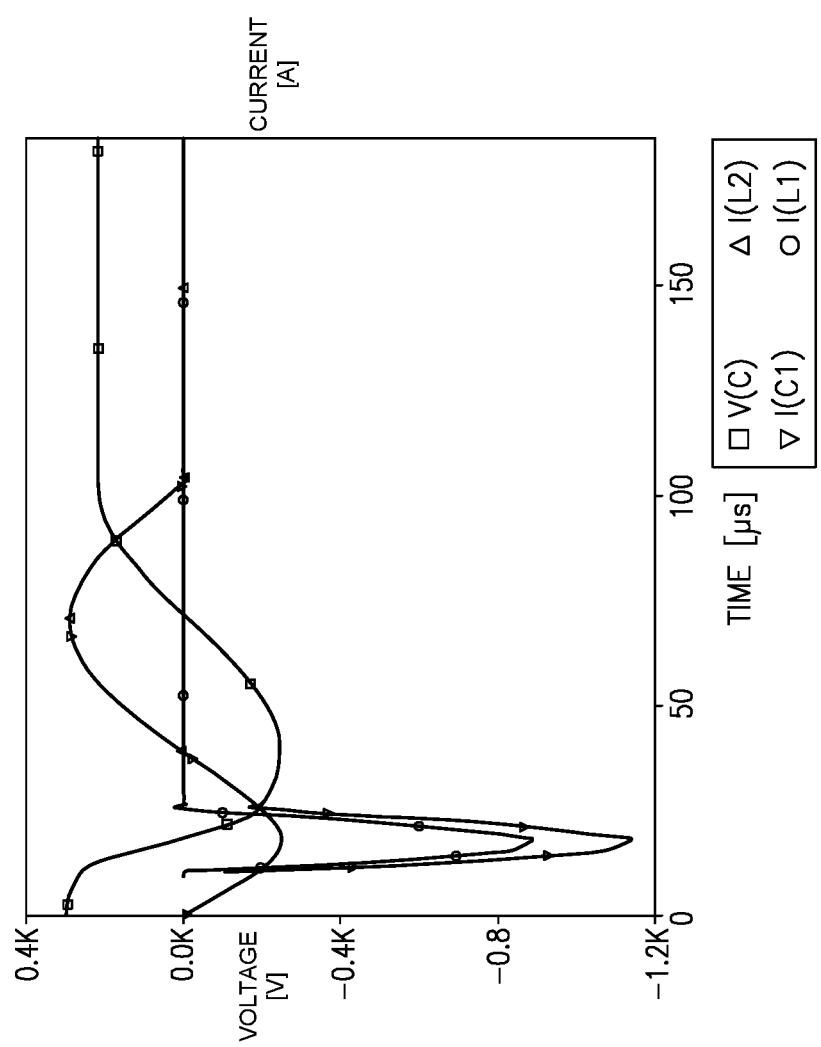
FIG. 9 is a graphical illustration showing pulse shapes which may be produced upon operation of the circuit shown in FIG. 5 in accordance with the parameters of another embodiment of the present invention.

Reference is now made to FIG. 9, which is a graphical illustration showing pulse shapes which may be produced upon operation of the circuit shown in FIG. 5 in accordance with one embodiment of the present invention. Switches Z2a and Z2b are opened between 0 and 103 µs, switch Z1a is opened between 10 and 42 µs, and switch Z1b is always closed. The result is a biphasic pulse in coil L2 between 0 and 103 µs, and a monophasic pulse in coil L1 between 10 and 26 µs. The capacitor voltage at the end of the cycle is more than 70% of its initial value.

This example may be implemented with either L1 or L2 or both attached to a body organ, at similar or different locations. The monophasic pulse in coil L1, with the smaller inductance, has a narrower pulse width with sharp current increase and higher peak current. If the two coils are applied to a body organ, a current pattern similar to I(C1) in FIG. 9 may be produced, with a relatively slow increase at the beginning (between 0 and 10 µs in this example), then a sharp increase, followed by a sharp decrease, then a slow decrease (between 26 and 38 µs), and then a current pulse in the opposite direction. This example may be generalized by opening Z1a and/or Z1b at different time points, i.e. during the $2^{nd}$ opposite phase, thus producing other or additional sharp pulses such as I(L1) in FIG. 9. The width of each pulse component may be varied by changing the coils' inductances, the resistances and/or the capacitances in the system.

Example 5

In another non-limiting example, capacitor C1 has C=25 µF, coil L1 has an inductance of 1 µH, coil L2 has an inductance of 16 µH, the resistances in the two circuits are R1=R2=0.05 Ohm, and the initial capacitor voltage is V(C1)=300 V, as in Example 4. However, the timing of the opening/closing of the switches is changed.

Figure 10:
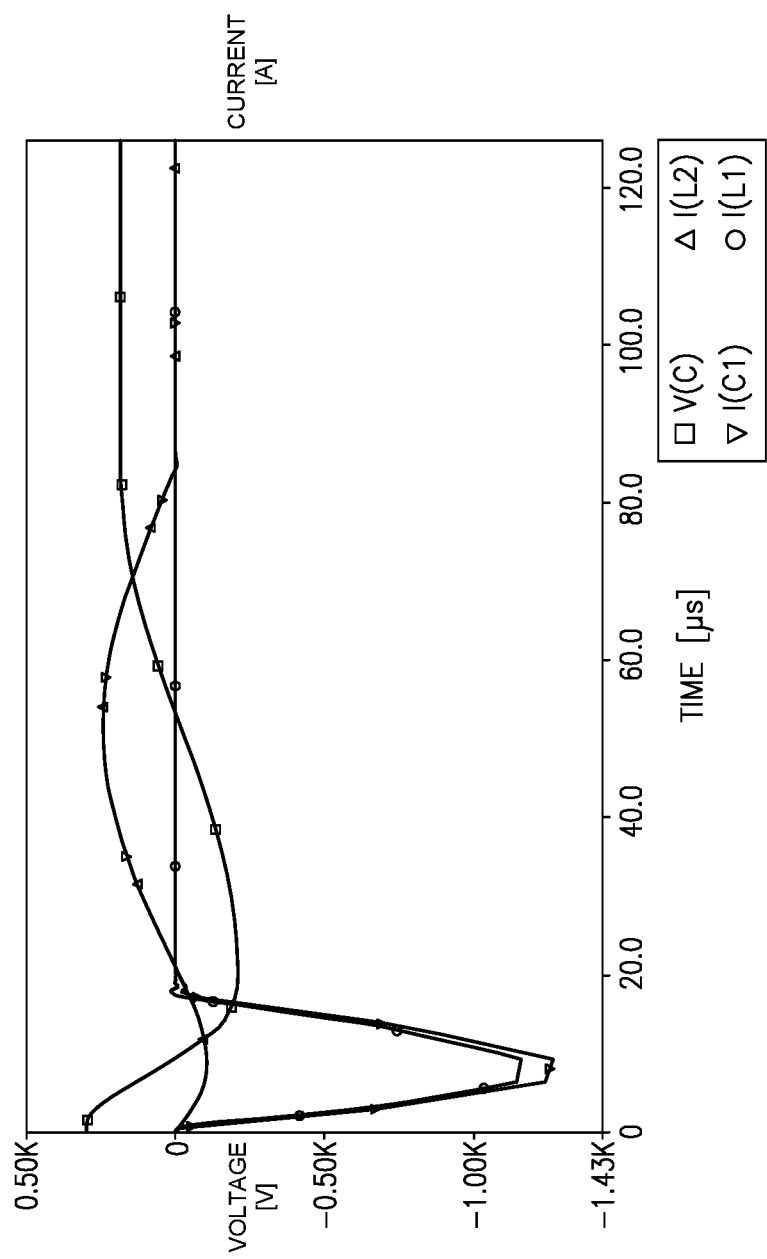
FIG. 10 is a graphical illustration showing pulse shapes which may be produced upon operation of the circuit shown in FIG. 5 in accordance with the parameters of another embodiment of the present invention.

Reference is now made to FIG. 10, which is a graphical illustration showing pulse shapes which may be produced upon operation of the circuit shown in FIG. 5 in accordance with the parameters of Example 5. In this example, the timing of the switches is similar to Example 4, except that switch Z1a is now open between 0 and 42 µs. The result is a biphasic pulse in coil L2 between 0 and 90 µs, and a monophasic pulse in coil L1, between 0 and 18 µs. The capacitor voltage at the end of cycle is now about 61% of its initial value, which is less than in previous examples. This is due to the fact that current flows through L1 during a larger fraction of the cycle, and the damping is larger in coils with smaller inductances, such as L1 in this case.

Again, one can implement this system with either L1 or L2 or both attached to a body organ, at similar or different locations.

Example 6

In another non-limiting example, capacitor C1 has C=25 µF, coil L1 has an inductance of 1 µH, coil L2 has an inductance of 16 µH, the resistances in the two circuits are R1=R2=0.05 Ohm, and the initial capacitor voltage is V(C1)=300 V, as in Examples 4, and 5. However, the timing of opening/closing of the switches is changed.

Figure 11:
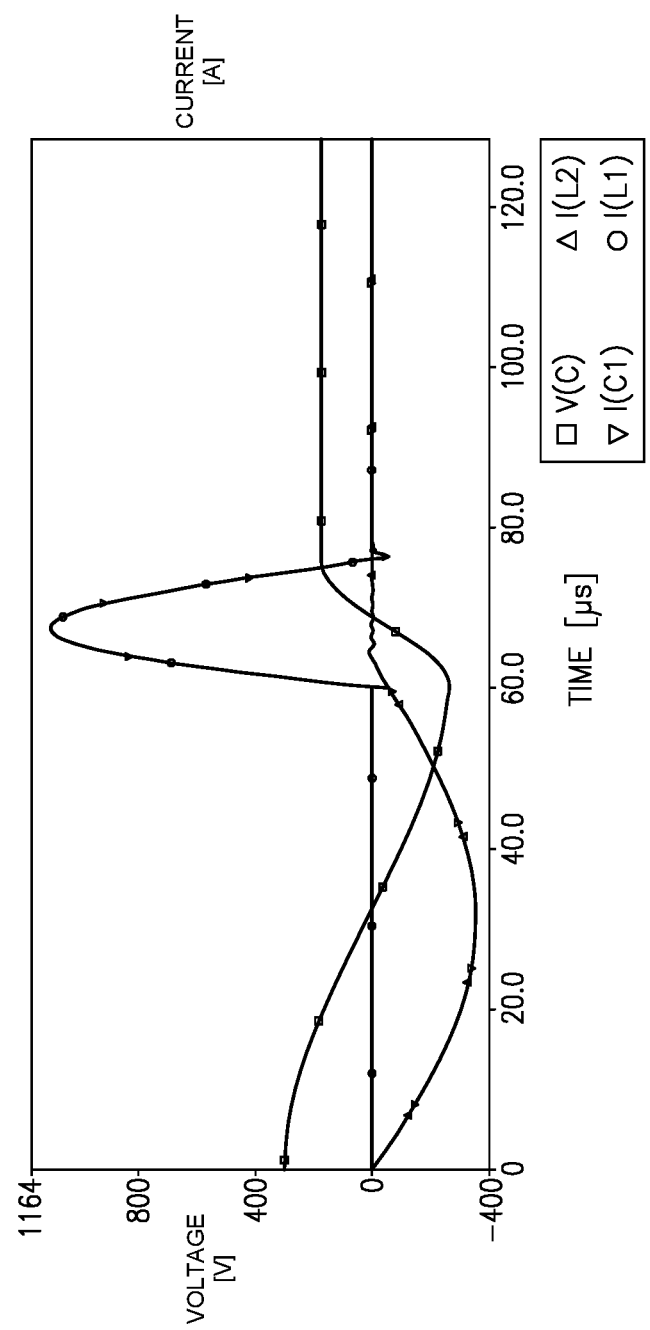
FIG. 11 is a graphical illustration showing pulse shapes which may be produced upon operation of the circuit shown in FIG. 5 in accordance with the parameters of another embodiment of the present invention.

Reference is now made to FIG. 11, which is a graphical illustration showing pulse shapes which may be produced upon operation of the circuit shown in FIG. 5 in accordance with the parameters of Example 6. In this example, switch Z2a is now opened between 0 and 64 µs, and switch Z1b is opened between 60 and 76 µs. The result is a monophasic pulse in coil L2 between 0 and 64 µs, and an opposite monophasic pulse in coil L1, between 60 and 76 µs. The capacitor voltage at the end of the cycle is now about 57% of its initial value, which is less than in previous examples.

Again, one can implement this system with either L1 or L2 or both coils with the same or opposite polarity, attached to a body organ, at similar or different locations.

Figure 12:
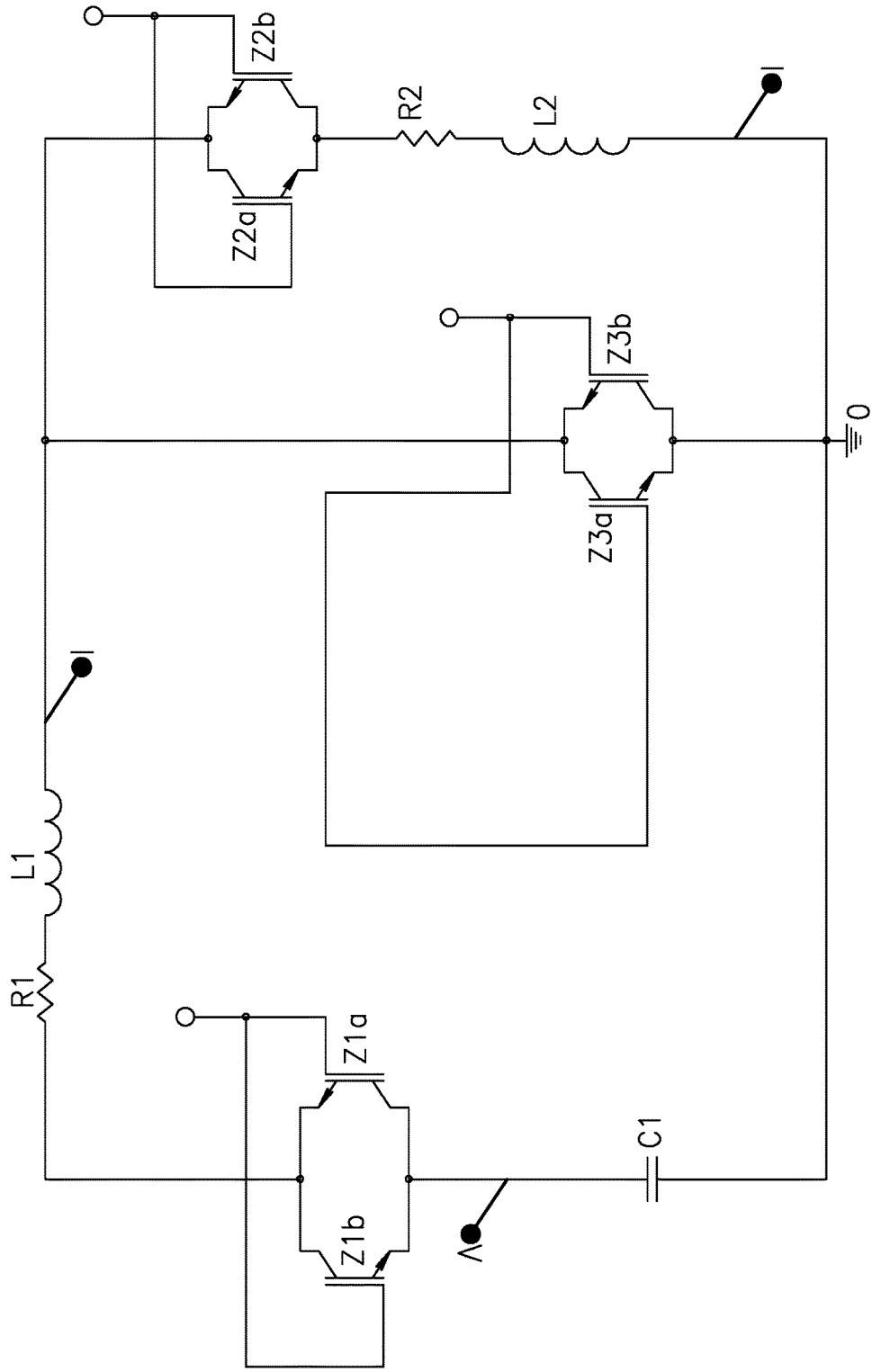
FIG. 12 is a circuit diagram in accordance with another embodiment of the present invention.

Reference is now made to FIG. 12, which is a circuit diagram in accordance with another embodiment of the present invention. In the embodiment shown in FIG. 12, two stimulating coils L1 and L2 are connected in series, with one capacitor C1 and six switches: Z1a, Z1b, Z2a, Z2b, Z3a and Z3b. In the embodiment shown in FIG. 12, switches Z1a, Z1b, Z2a, Z2b, Z3a and Z3b are IGBTs; however, any suitable switches may be used. The timing of opening or closing of each switch is controllable by the user.

Several examples using the circuit of FIG. 12 are now described.

Example 7

In this example, capacitor C1 has C=25 uF, coil L1 has an inductance of =16 µH, coil L2 has an inductance of 150 µH, the resistances in the two coils are R1=R2=0.05 Ohm, and the initial capacitor voltage is V(C1)=300 V. The timing of opening/closing of the switches is controllable by the user.

Figure 13:
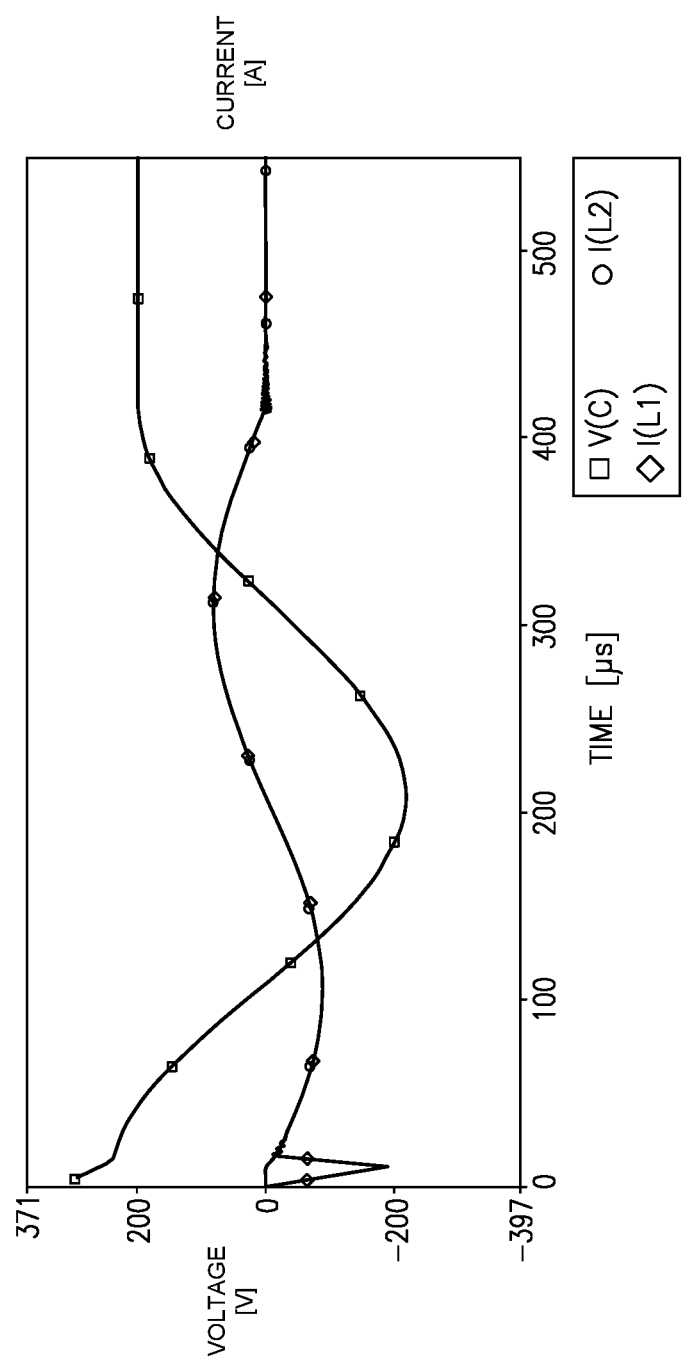
FIG. 13 is a graphical illustration showing pulse shapes which may be produced upon operation of the circuit shown in FIG. 12 in accordance with the parameters of one embodiment of the present invention.

Reference is now made to FIG. 13, which is a graphical illustration showing pulse shapes which may be produced upon operation of the circuit shown in FIG. 12 in accordance with the parameters of Example 7. In this example, switches Z1a, Z1b, Z2a and Z2b are opened between 0 and 415 µs, switch Z3a is opened at 0 µs and closed at 10 µs, and Z3b is always closed. The result is a pulse which increases sharply in L1 between 0 and 10 µs, decreases very sharply, followed by a biphasic pulse with a long pulse width and lower current amplitude, typical of higher inductance coils. This occurs because after 10 µs, coils L1 and L2 are connected in series, and the total inductance is $L_T$=L1+L2=166 uH. In coil L2 there is almost no current until 10 µs, followed by a biphasic pulse. The capacitor voltage at the end of cycle is about 66% of its initial value.

Again, one can implement this system with either L1 or L2 or both attached to a body organ, at similar or different locations.

Example 8

In this example, as in Example 7, capacitor C1 has C=25 uF, coil L1 has an inductance of =16 µH, coil L2 has an inductance of 150 µH, the resistances in the two coils are R1=R2=0.05 Ohm, and the initial capacitor voltage is V(C1)=300 V. The timing of opening/closing of the switches is controllable by the user.

Figure 14:
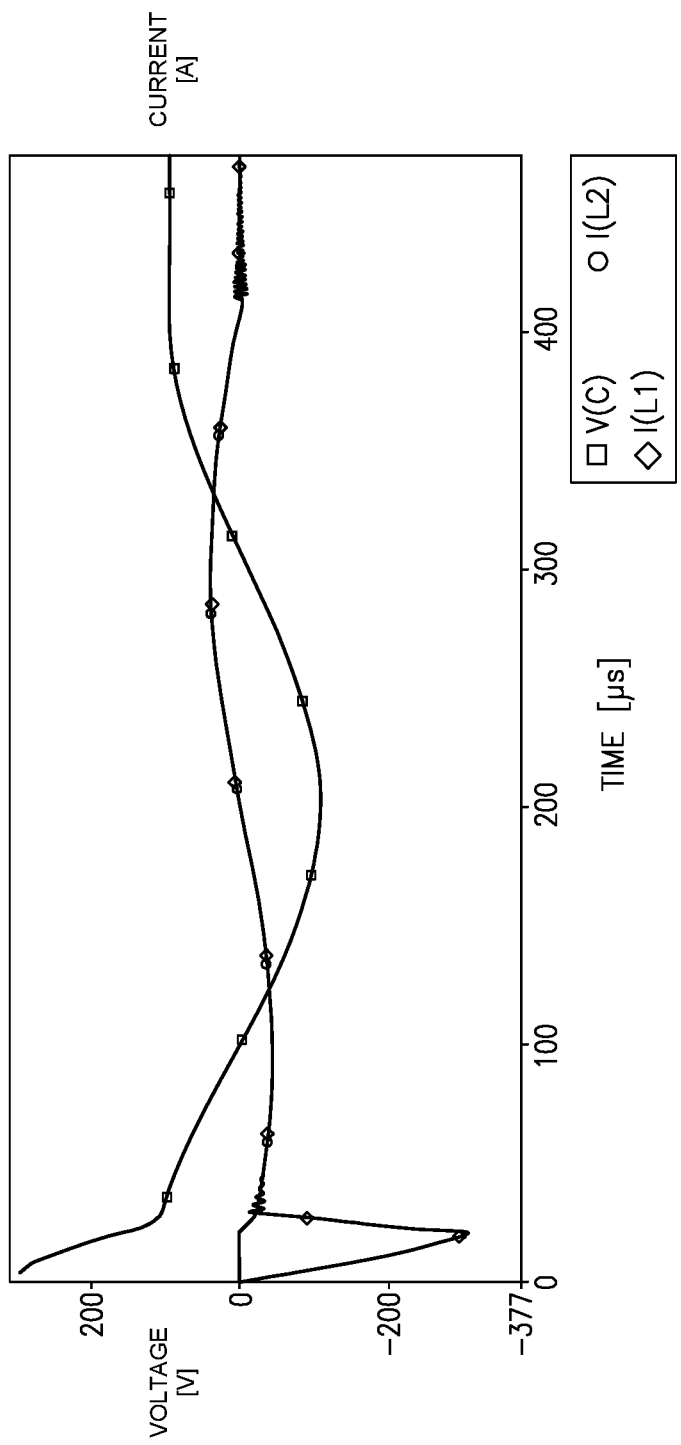
FIG. 14 is a graphical illustration showing pulse shapes which may be produced upon operation of the circuit shown in FIG. 12 in accordance with the parameters of one embodiment of the present invention.

Reference is now made to FIG. 14, which is a graphical illustration showing pulse shapes which may be produced upon operation of the circuit shown in FIG. 12 in accordance with the parameters of Example 8. Switches Z1a, Z1b, Z2a and Z2b are opened between 0 and 415 µs, switch Z3a is opened at 0 µs and closed at 20 µs (as opposed to 10 µs as in Example 7), and Z3b is always closed. In this example, the current peak in coil L1 is much larger than in Example 7. Yet the capacitor voltage at the end of cycle is only about 30% of its initial value.

Example 9

In this example, capacitor C1 has C=180 μF (and not 25 μF, as in Examples 7 and 8), coil L1 has an inductance of =16 μH, coil L2 has an inductance of 150 μH, the resistances in the two coils are R1=R2=0.05 Ohm, and the initial capacitor voltage is V(C1)=300 V. The timing of opening/closing of the switches is controllable by the user. This example is designed to demonstrate that an increase in the fraction of electric energy which is returned to the capacitor may be obtained by increasing the capacitance.

Figure 15:
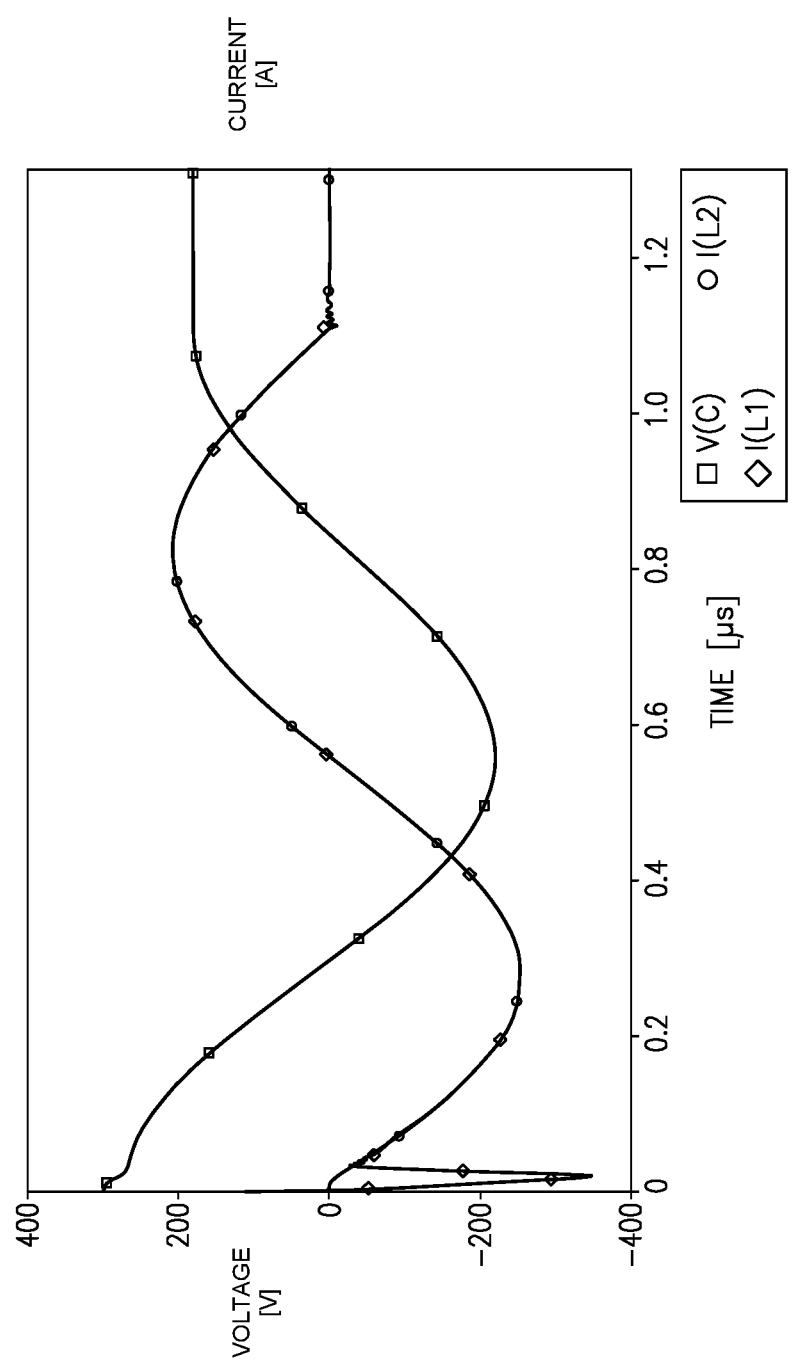
FIG. 15 is a graphical illustration showing pulse shapes which may be produced upon operation of the circuit shown in FIG. 12 in accordance with the parameters of another embodiment of the present invention.

Reference is now made to FIG. 15, which is a graphical illustration showing pulse shapes which may be produced upon operation of the circuit shown in FIG. 12 in accordance with the parameters of Example 9. In this example, the peak current in coil L1 at 20 μs is larger than in Example 8 (FIG. 14), and the capacitor voltage at the end of cycle is about 60% of its initial value. The energy fraction returned to the capacitor can thus be improved by increasing the capacitance.

Figure 16:
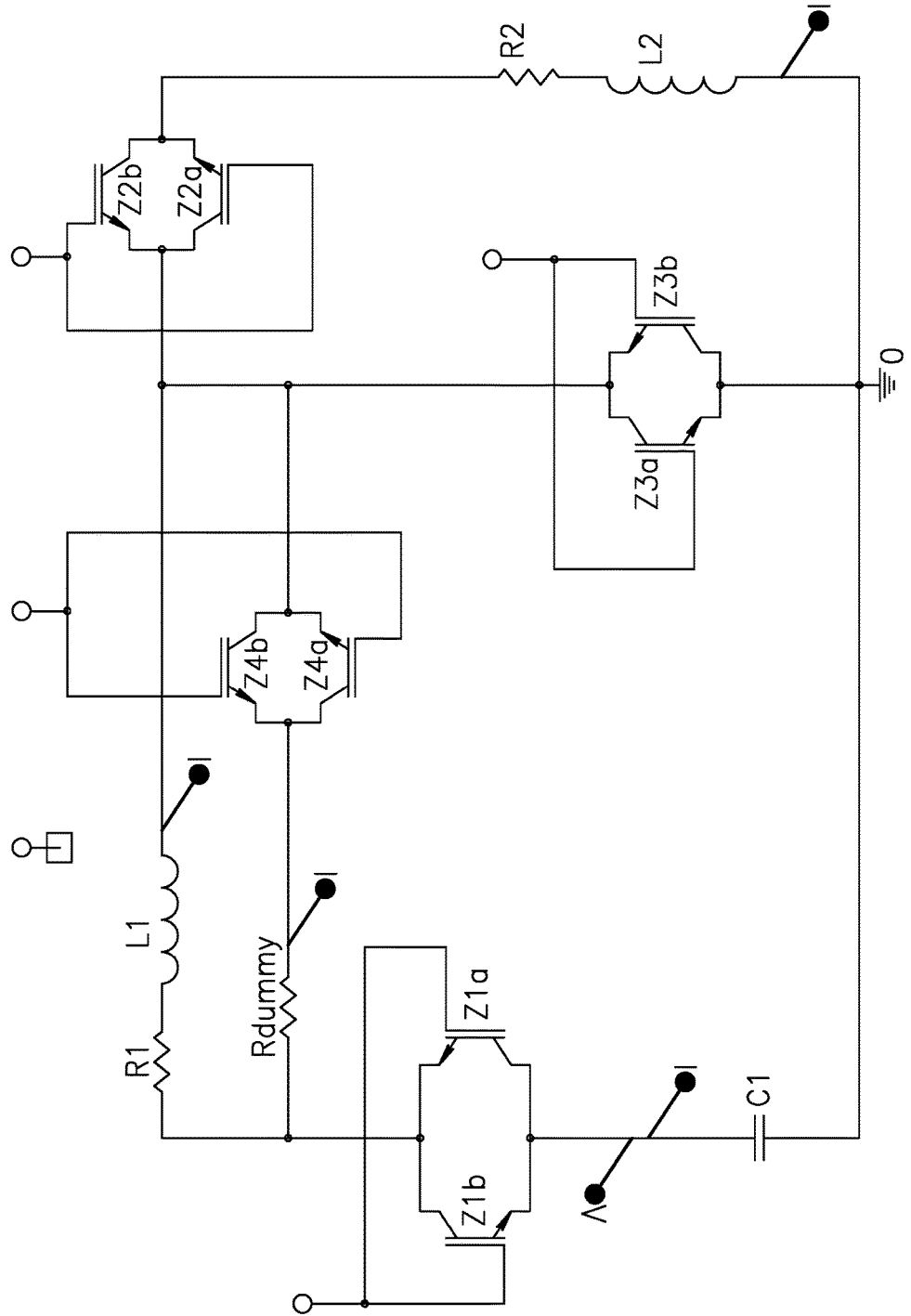
FIG. 16 is a circuit diagram in accordance with another embodiment of the present invention.

Reference is now made to FIG. 16, which is a circuit diagram in accordance with another embodiment of the present invention. In the embodiment shown in FIG. 16, two stimulating coils L1 and L2 are connected in series, with one capacitor C1 and eight switches: Z1a, Z1b, Z2a, Z2b, Z3a, Z3b, Z4a and Z4b. In the embodiment shown in FIG. 16, switches Z1a, Z1b, Z2a, Z2b, Z3a, Z3b, Z4a and Z4b are IGBTs; however, any suitable switches may be used. The timing of opening or closing of each switch is controllable by the user.

Several examples using the circuit of FIG. 16 are now described.

Example 10

In this example, capacitor C1 has a capacitance of 180 μF, coil L1 has an inductance of 16 μH, coil L2 has an inductance of 150 μH, the resistances in the two coils are R1=R2=0.05 Ohm, and the initial capacitor voltage V(C1) is 300 V. Switches Z4a and Z4b are connected in parallel to coil L1, and switches Z3a and Z3b are connected in parallel to coil L2.

Figure 17:
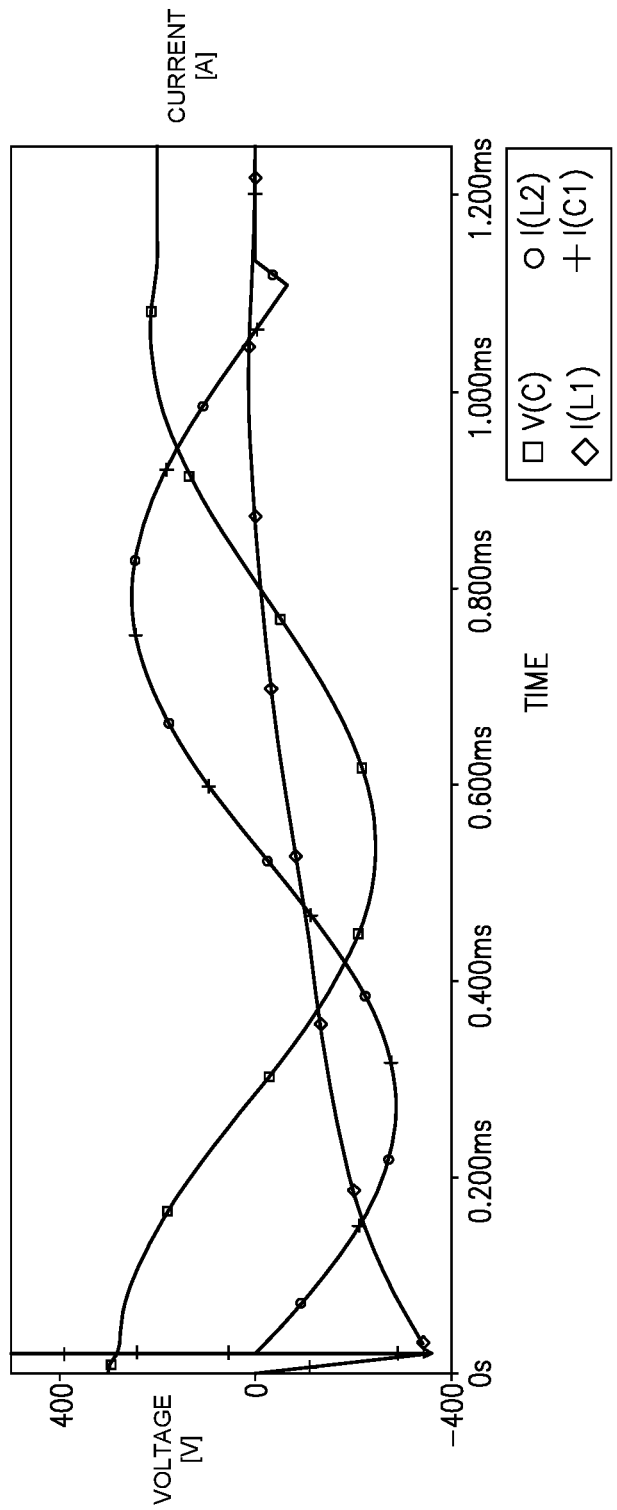
FIG. 17 is a graphical illustration showing pulse shapes which may be produced upon operation of the circuit shown in FIG. 16 in accordance with the parameters of one embodiment of the present invention.

Reference is now made to FIG. 17, which is a graphical illustration showing pulse shapes which may be produced upon operation of the circuit shown in FIG. 16 in accordance with the parameters of Example 10. In this example, switches Z3a and Z3b are opened at 0 μs and closed at 20 μs, and switches Z4a and Z4b are closed until 20 μs and then opened. As a result, the current flows between 0 and 20 μs through coil L1 and not through coil L2. After 20 μs, the current from the capacitor flows through switch Z4a and coil L2, and the current of L1 decays exponentially through switch Z4b. The result is a current pulse which increases sharply in L1 between 0 and 20 μs, and then decays exponentially. In coil L2 a biphasic pulse is produced. The capacitor voltage at the end of the cycle is about 70% of its initial value, which makes repetitive activation feasible. The exponential decay in coil L1 current may reduce voltage losses and also transient voltage spikes on switches.

Again, one can implement this system with either L1 or L2 or both attached to a body organ, at similar or different locations.

Example 11

In this example, capacitor C1 has a capacitance of 180 μF, coil L1 has an inductance of 16 μH, coil L2 has an inductance of 150 μH, the resistances in the two coils are R1=R2=0.05 Ohm, and the initial capacitor voltage V(C1) is 300 V. Switches Z4a and Z4b are connected in parallel to coil L1, and switches Z3a and Z3b are connected in parallel to coil L2.

Figure 18:
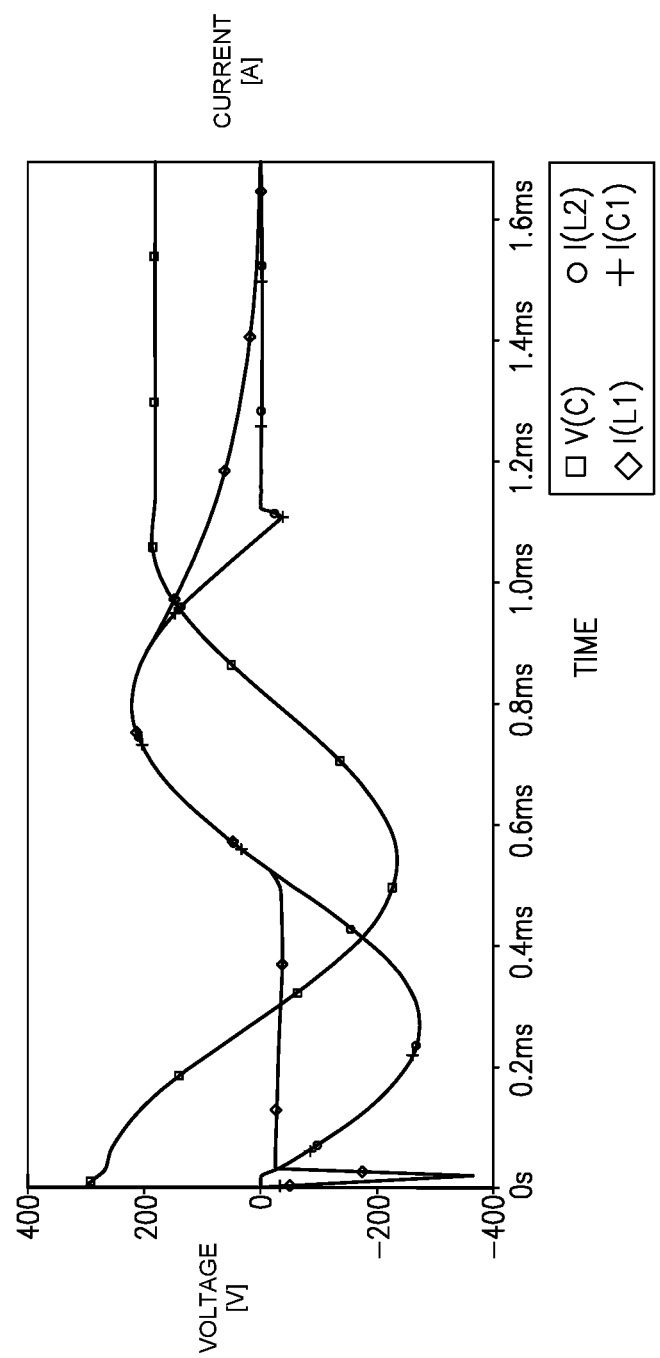
FIG. 18 is a graphical illustration showing pulse shapes which may be produced upon operation of the circuit shown in FIG. 16 in accordance with the parameters of another embodiment of the present invention.

Reference is now made to FIG. 18, which is a graphical illustration showing pulse shapes which may be produced upon operation of the circuit shown in FIG. 16 in accordance with the parameters of Example 11. In this example, switches Z3a and Z3b are opened at 0 μs and closed at 20 μs, and switch Z4a is closed until 20 μs and then opened. Switch Z4b is always closed. As a result, the pulse shape induced in coil L1 is different. The current decays sharply at 20 μs to a low constant value, at about 550 μs a $2^{nd}$ phase in an opposite direction is produced, similar to coil L2, and at about 950 μs, after the capacitor voltage changes sign, the current in L1 decays exponentially. In coil L2 a biphasic pulse is induced. The capacitor voltage at the end of the cycle is about 62% of its initial value.

Again, one can implement this system with either L1 or L2 or both attached to a body organ, at similar or different locations. The time interval of constant current in coil L1 (between 20 and about 500 μs in the example of FIG. 18), can be varied by changing the inductance of L2 and/or the capacitance. In this way, hyper-polarizing and depolarizing pulses with variable intervals between them may be produced in a neuronal tissue.

Example 12

In this non limiting example, capacitor C1 has C=180 μF, coil L1 has an inductance of 16 μH, coil L2 has an inductance of 150 μH, the resistances in the two coils are R1=R2=0.05 Ohm, and the initial capacitor voltage V(C1)=300 V. Switches Z4a and Z4b are connected in parallel to coil L1, and switches Z3a and Z3b are connected in parallel to coil L2.

Figure 19:
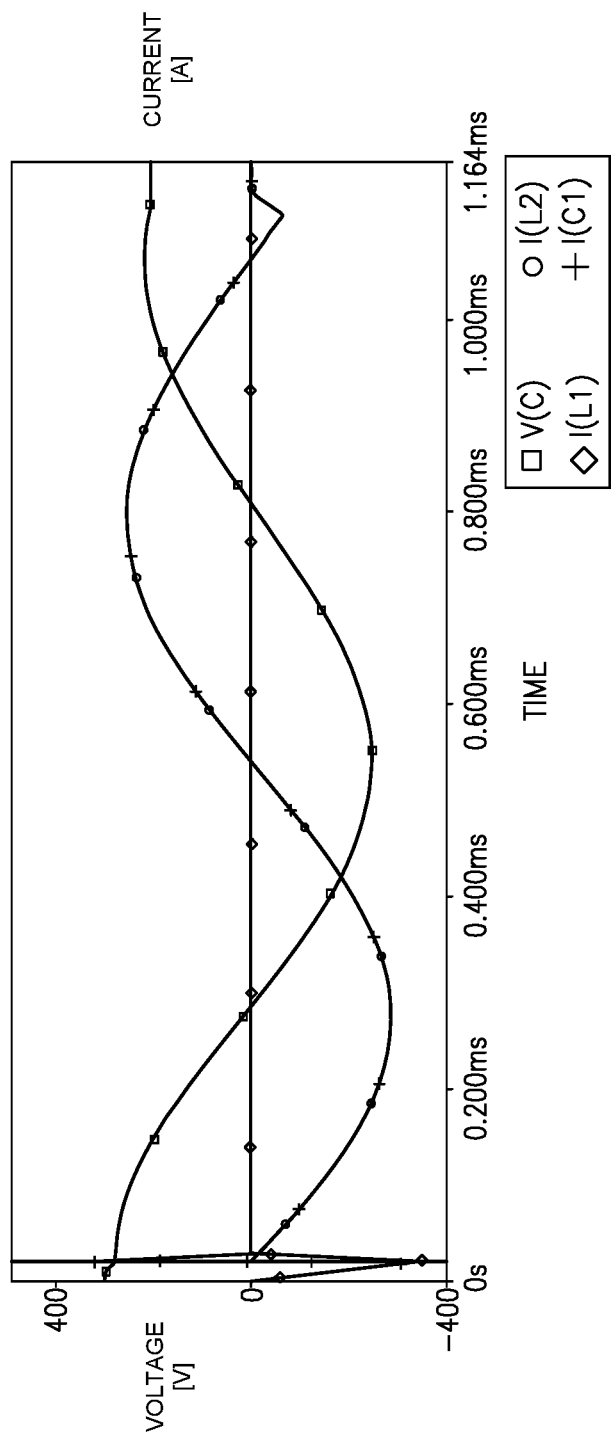
FIG. 19 is a graphical illustration showing pulse shapes which may be produced upon operation of the circuit shown in FIG. 16 in accordance with the parameters of another embodiment of the present invention.

Reference is now made to FIG. 19, which is a graphical illustration showing pulse shapes which may be produced upon operation of the circuit shown in FIG. 16 in accordance with the parameters of Example 12. Switches Z1a, Z3a and Z3b are opened between 0 and 20 μs, switches Z4a and Z4b are opened between 20 and 1100 μs, and switches Z2a and Z2b are opened between 0 and 1100 μs. The result is that between 0 and 20 μs current flows through L1 and minimally through L2, and after 20 μs current flows only through L2 and not through L1, producing a biphasic pulse. This result could be implemented with a simpler circuit, with three switches and coils L1 and L2 connected in parallel. The resulting pulse in L1 would be similar to that shown in FIG. 19, but after 20 μs the current would decrease sharply to zero. The capacitor voltage at the end of cycle is about 70% of its initial value. Hence it is possible to produce the pulse shape of L1, in a high frequency repetitive operation. Note that by varying the closing time, capacitance and initial capacitor voltage, it may be possible to produce with this method a great variety of pulse shapes of the electric field, including almost any rectangular pulse shape.

Again, one can implement this system with either L1 or L2 or both attached to a body organ, at similar or different locations.

Example 13

In this non-limiting example, capacitor C1 has C=180 μF, coil L1 has an inductance of 16 μH, coil L2 has an inductance of 150 μH, the resistances in the two coils are R1=R2=0.05 Ohm, and the initial capacitor voltage V(C1)=300 V. Switches Z4a and Z4b are connected in parallel to coil L1, and switches Z3a and Z3b are connected in parallel to coil L2.

Figure 20:
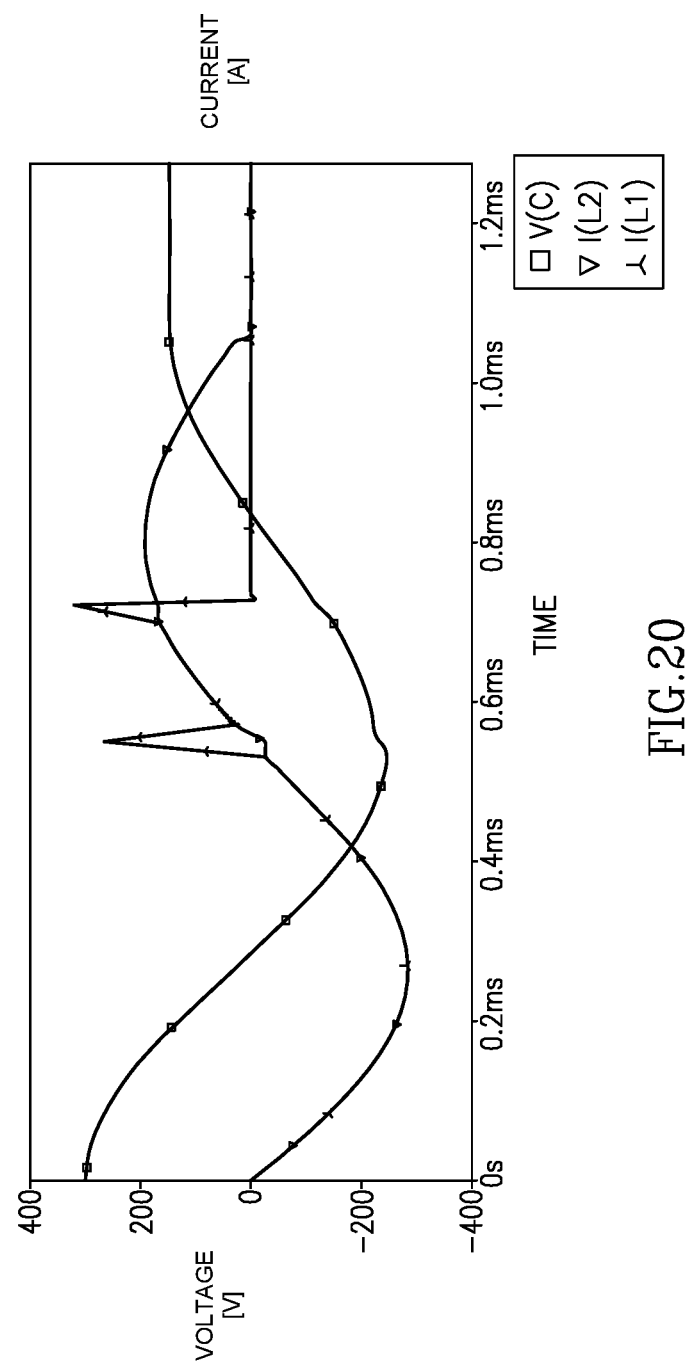
FIG. 20 is a graphical illustration showing pulse shapes which may be produced upon operation of the circuit shown in FIG. 16 in accordance with the parameters of another embodiment of the present invention.

Reference is now made to FIG. 20, which is a graphical illustration showing pulse shapes which may be produced upon operation of the circuit shown in FIG. 16 in accordance with the parameters of Example 13. In this example, the current flows during a $1^{st}$ phase through both coils between 0 and 530 µs. Between 530 and 550 µs, and also between 700 and 720 µs, current flows mostly through coil L1. Hence during these two periods sharp pulses are produced in coil L1. Between 550 and 700 µs, current flows through both coils in series. After 720 µs, switches Z1b and Z3b are closed, the current in L1 decays sharply to zero, and current flows only through L2. The capacitor voltage at the end of cycle is about 50% of its initial value.

The position in time of the two sharp current pulses (between 530 and 550 µs and between 700 and 720 µs, in the example of FIG. 20) and the time interval between them can be controlled and varied, by controlling the opening and closing times of the switches. In addition any number of sharp pulses can be produced in a similar way. Apart from that, such pulses may be produced during either the $1^{st}$ or the $2^{nd}$ phase, or during both of them. Hence there is a means to produce a great variety of depolarizing and/or hyper-polarizing pulse shapes.

Again, one can implement this system with either L1 or L2 or both attached to a body organ, at similar or different locations.

Example 14

In this non-limiting example, as in Example 13, capacitor C1 has C=180 µF, coil L1 has an inductance of 16 µH, coil L2 has an inductance of 150 µH, the resistances in the two coils are R1=R2=0.05 Ohm, and the initial capacitor voltage V(C1)=300 V. Switches Z4a and Z4b are connected in parallel to coil L1, and switches Z3a and Z3b are connected in parallel to coil L2.

Figure 21:
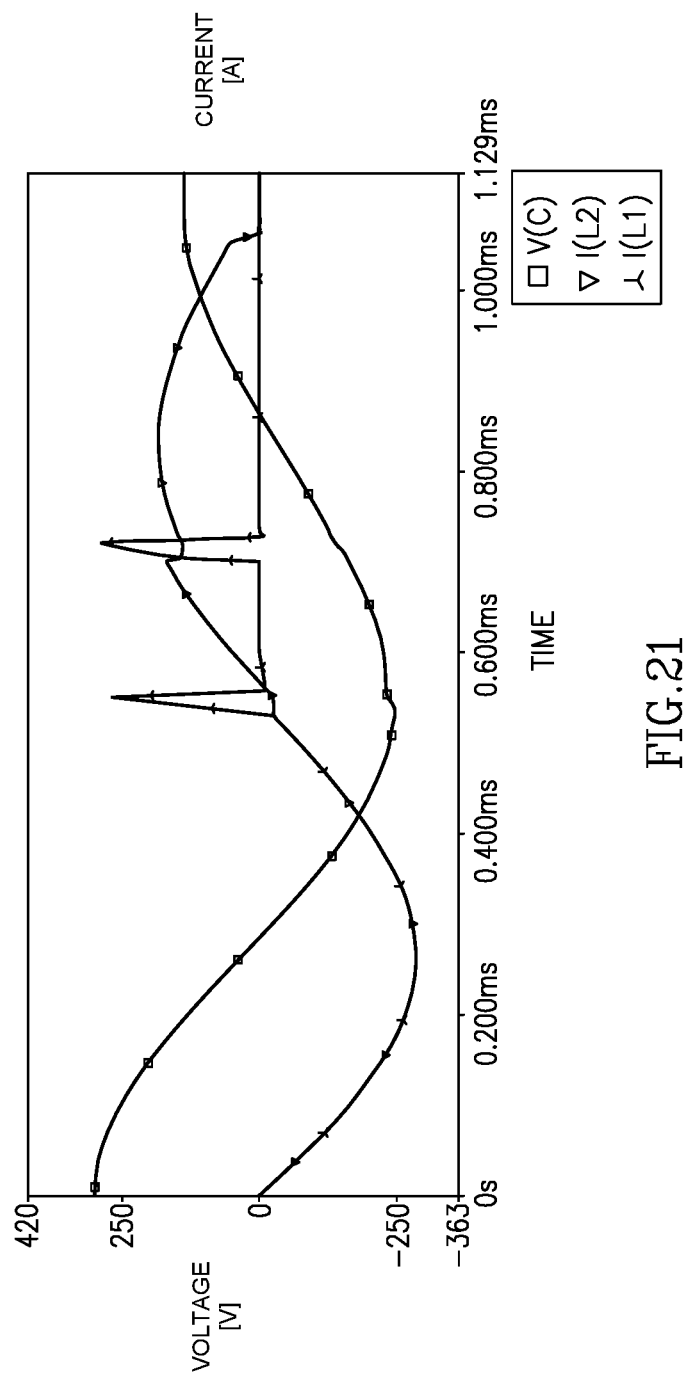
FIG. 21 is a graphical illustration showing pulse shapes which may be produced upon operation of the circuit shown in FIG. 16 in accordance with the parameters of another embodiment of the present invention.

Reference is now made to FIG. 21, which is a graphical illustration showing pulse shapes which may be produced upon operation of the circuit shown in FIG. 16 in accordance with the parameters of Example 14. In this example, the current flows during a $1^{st}$ phase through both coils between 0 and 530 µs. Between 550 and 700 µs switch Z4b is open while switches Z1b and Z3b are closed, thus the current flows only through coil L2, and the current in L1 is zero. After 720 µs, switches Z1b and Z3b are closed, the current in L1 decays sharply to zero, and current flows only through L2. The capacitor voltage at the end of cycle is about 50% of its initial value.

Example 15

In this non-limiting example, as in Examples 13 and 14, capacitor C1 has C=180 µF, coil L1 has an inductance of 16 pH, coil L2 has an inductance of 150 µH, the resistances in the two coils are R1=R2=0.05 Ohm, and the initial capacitor voltage V(C1)=300 V. Switches Z4a and Z4b are connected in parallel to coil L1, and switches Z3a and Z3b are connected in parallel to coil L2.

Figure 22:
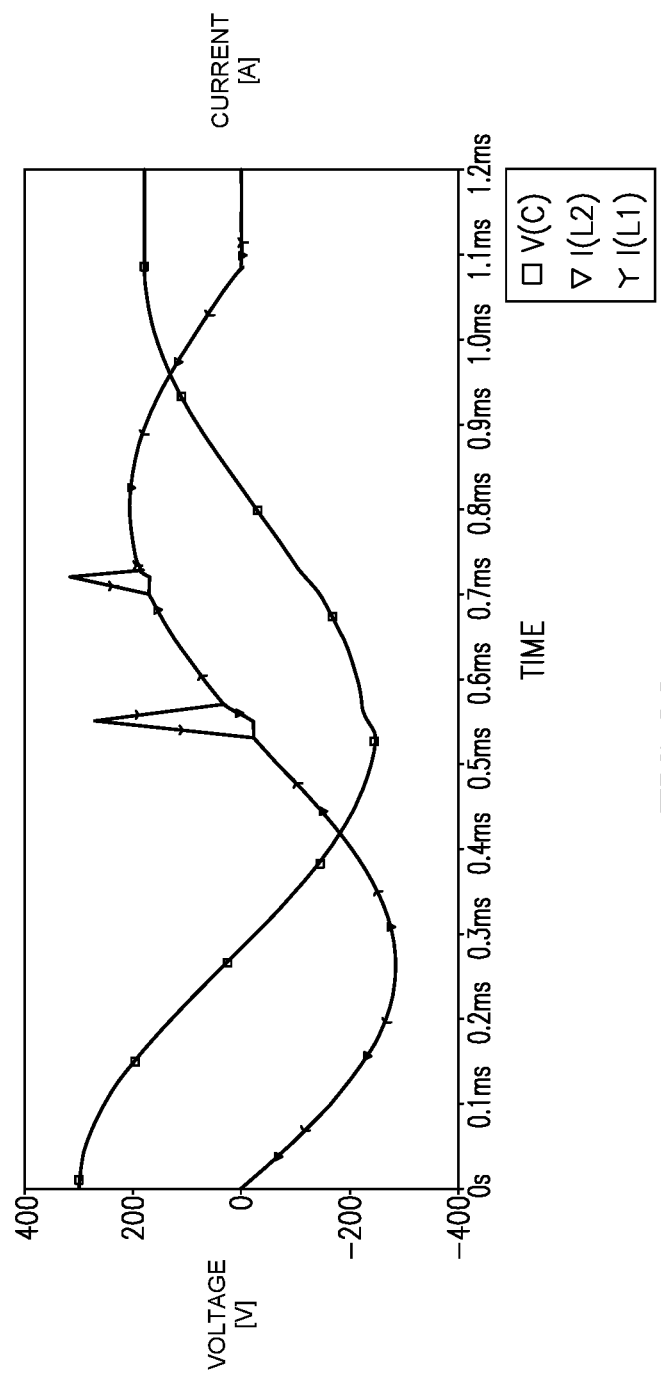
FIG. 22 is a graphical illustration showing pulse shapes which may be produced upon operation of the circuit shown in FIG. 16 in accordance with the parameters of another embodiment of the present invention.

Reference is now made to FIG. 22, which is a graphical illustration showing pulse shapes which may be produced upon operation of the circuit shown in FIG. 16 in accordance with the parameters of Example 15. In this example, the current flows during a $1^{st}$ phase through both coils between 0 and 530 µs. Between 550 and 700 µs, and also after 720 µs, switch Z1b is opened, and Z3b is closed, hence the current flows through both coils in series. The capacitor voltage at the end of cycle is about 60% of its initial value.

Switches Z4a and Z4b are always closed in these examples and as such, they are unnecessary for the implementation of this example. Yet, in another embodiment, switch Z4a can be opened for some period between 0 and 500 µs, possibly in combination with closing of switch Z1a, thus altering the pulse shapes during the $1^{st}$ phase.

Again, one can implement each of the above examples with either L1 or L2 or both attached to a body organ, at similar or different locations.

Figure 23:
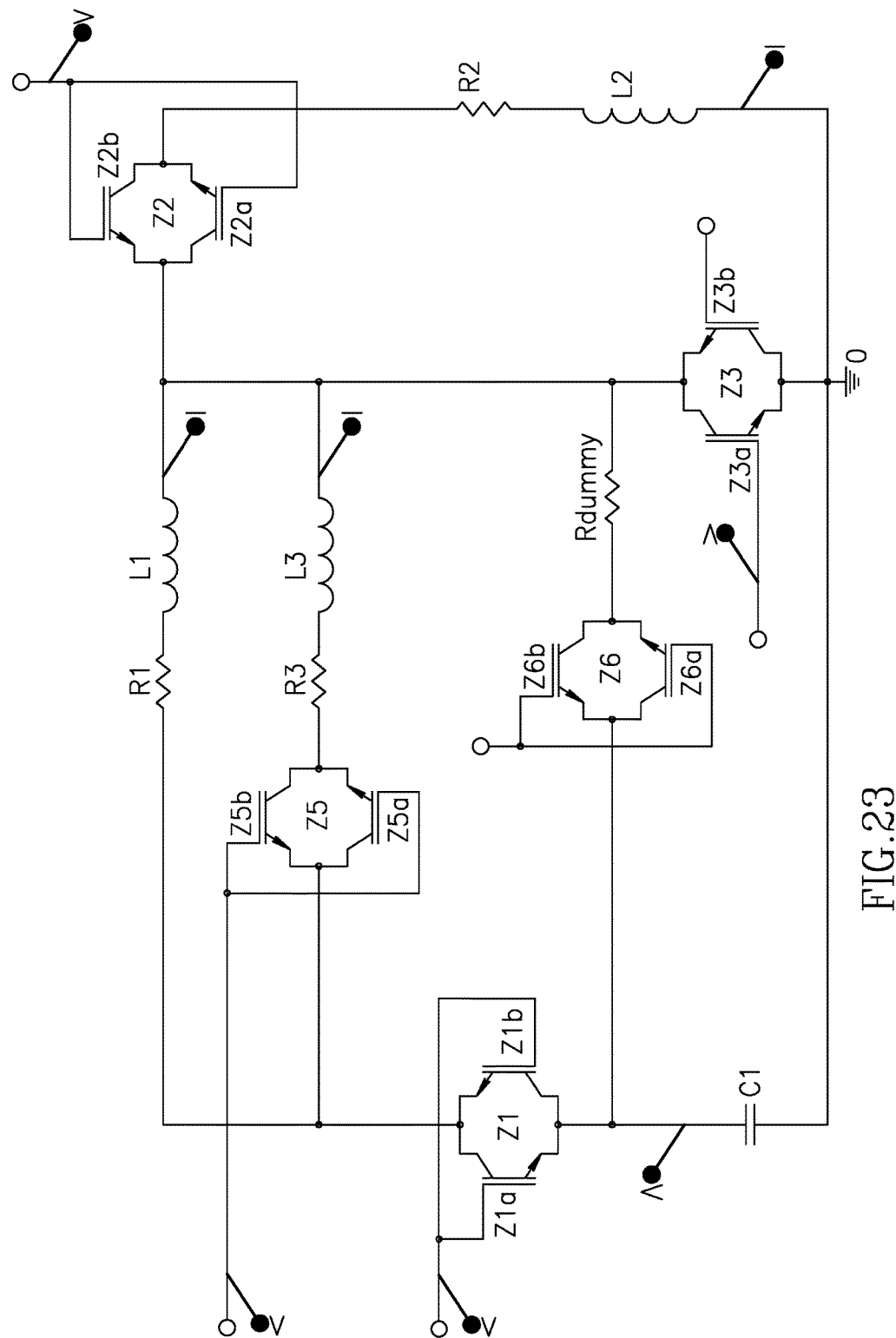
FIG. 23 is a circuit diagram in accordance with another embodiment of the present invention.

Reference is now made to FIG. 23, which is a circuit diagram in accordance with yet additional embodiments of the present invention. In the embodiment shown in FIG. 23, three stimulating coils L1, L2 and L3 are connected, with coils L1 and L3 connected in parallel, and coil L2 connected to coils L1 and L3 in series. The circuit also includes one capacitor C1 and ten switches: Z1a, Z1b, Z2a, Z2b, Z3a, Z3b, Z5a, Z5b, Z6a and Z6b. In the embodiment shown in FIG. 23, switches Z1a, Z1b, Z2a, Z2b, Z3a, Z3b, Z5a, Z5b, Z6a and Z6b are IGBTs; however, any suitable switches may be used. The timing of opening or closing of each switch is controllable by the user.

Example 16

In this non-limiting example the capacitor has C=25 µF, coil L1 has an inductance of 16 µH, coil L2 has an inductance of 150 µH, and coil L3 has an inductance of 1 µH, the resistances in the three coils are R1=R2=R3=0.05 Ohm, and the initial capacitor voltage V(C1)=300 V. Switches Z6a and Z6b are connected in parallel to coils L1 and L3, and switches Z3a and Z3b are connected in parallel to coil L2.

Figure 24:
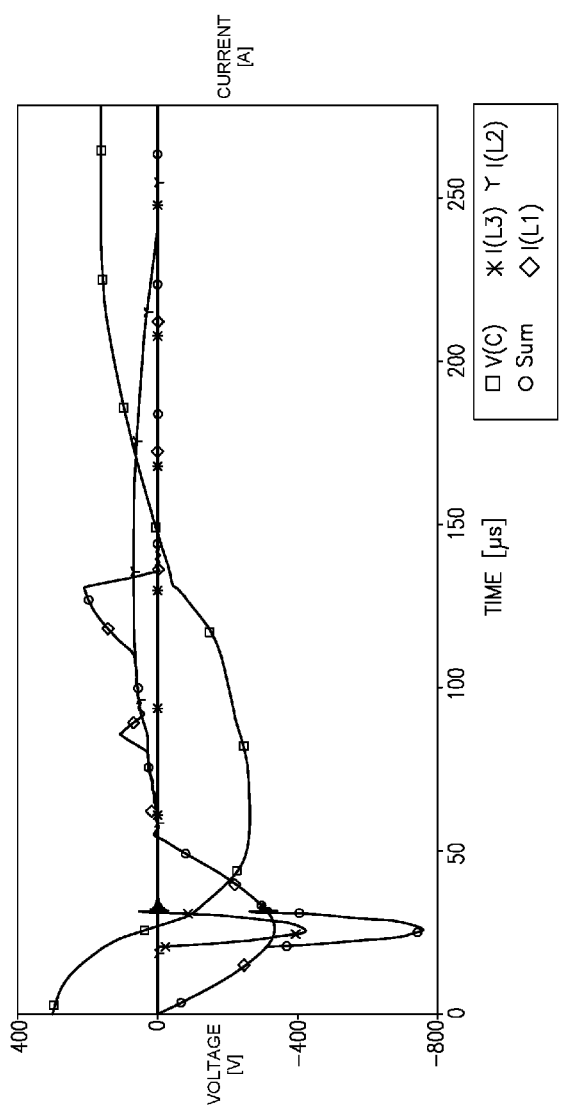
FIG. 24 is a graphical illustration showing pulse shapes which may be produced upon operation of the circuit shown in FIG. 23 in accordance with the parameters of one embodiment of the present invention.

Reference is now made to FIG. 24, which is a graphical illustration showing pulse shapes which may be produced upon operation of the circuit shown in FIG. 23 in accordance with the parameters of Example 16. The current flows initially through coil L1. Between 20 and 35 µs, switch Z5 is opened and current flows in parallel through L1 and L3. Between 35 and 60 µs current flows only through L1. After 60 µs, in $2^{nd}$ phase, current flows through both L1 and L2. Between 80 and 85 µs, and between 110 and 130 µs, switch Z3b is open, hence current flows mostly through L1. After 130 µs Z1 is closed and Z6 is opened, hence the current in L1 decays sharply, and current flows through L2 and recharges the capacitor. The capacitor voltage at the end of the cycle is over 50% of its initial value.

The position in time of the sharp pulse through L3 during the $1^{st}$ phase (between 20 and 35 µs), and/or of the two sharp current pulses through L1 during the $2^{nd}$ phase (between 80 and 85 µs and between 110 and 130 µs), and the time intervals between them, can be controlled and varied, by controlling the opening and closing times of the switches. In addition any number of sharp pulses can be produced in a similar way. Apart from that, such pulses may be produced during either the $1^{st}$ or the $2^{nd}$ phase, or during both of them. Hence there is a means to produce a great variety of depolarizing and/or hyper-polarizing pulse shapes.

Again, one can implement this system with either L1 and/or L2 and/or L3 attached to a body organ, at similar or different locations. In addition, such a system may be implemented with different coil inductances, resistances, capacitance and initial voltage.

Figure 25:
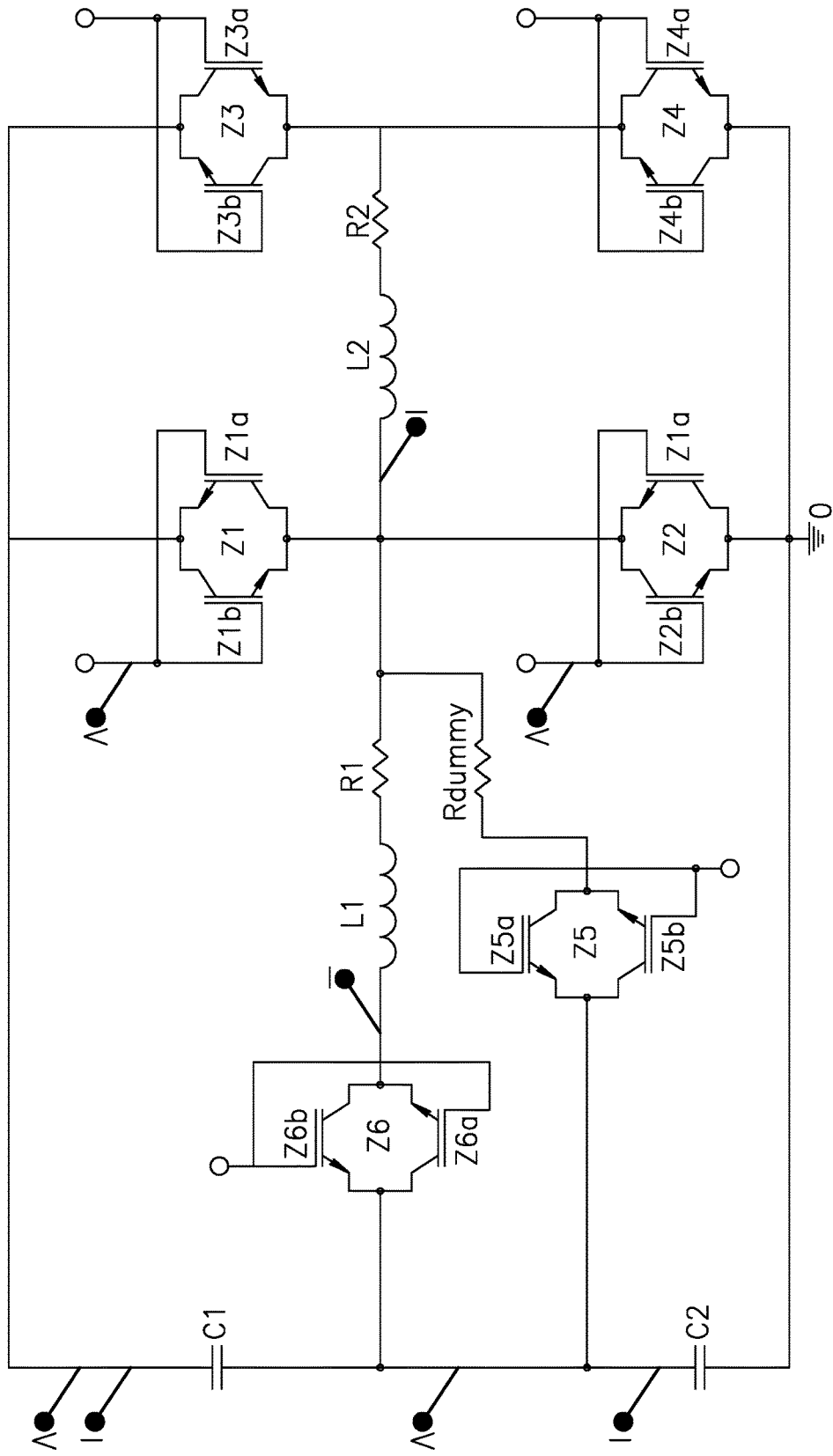
FIG. 25 is a circuit diagram in accordance with another embodiment of the present invention.

Reference is now made to FIG. 25, which is a circuit diagram in accordance with yet additional embodiments of the present invention. In the embodiment shown in FIG. 25, two stimulating coils L1 and L2 are connected in series, two capacitors C1 and C2 are connected in series, and there are twelve switches: Z1a, Z1b, Z2a, Z2b, Z3a, Z3b, Z4a, Z4b, Z5a, Z5b, Z6a and Z6b. In the embodiment shown in FIG. 25, switches Z1a, Z1b, Z2a, Z2b, Z3a, Z3b, Z4a, Z4b, Z5a, Z5b, Z6a and Z6b are IGBTs; however, any suitable switches may be used. The timing of opening or closing of each switch is controllable by the user.

Example 17

In this non-limiting example, the capacitors have capacitances of C1=180 µF and C2=700 µF, coil L1 has an inductance of 16 µH, coil L2 has an inductance of 150 µH, the resistances in the two coils are R1=R2=0.05 Ohm, and the initial capacitor voltages are V(C1)=300 V and V(C2)=400 V. Hence the voltages on the negative and positive poles of C1 are 400 V and 700 V, respectively. Switches Z1a/b and Z2a/b couple coil L1 with capacitors C1 and C2, respectively. Switches Z3a/b and Z4a/b couple coil L2 with capacitors C1 and C2, respectively. Switches Z5a/b are connected in parallel to coil L1.

Figure 26:
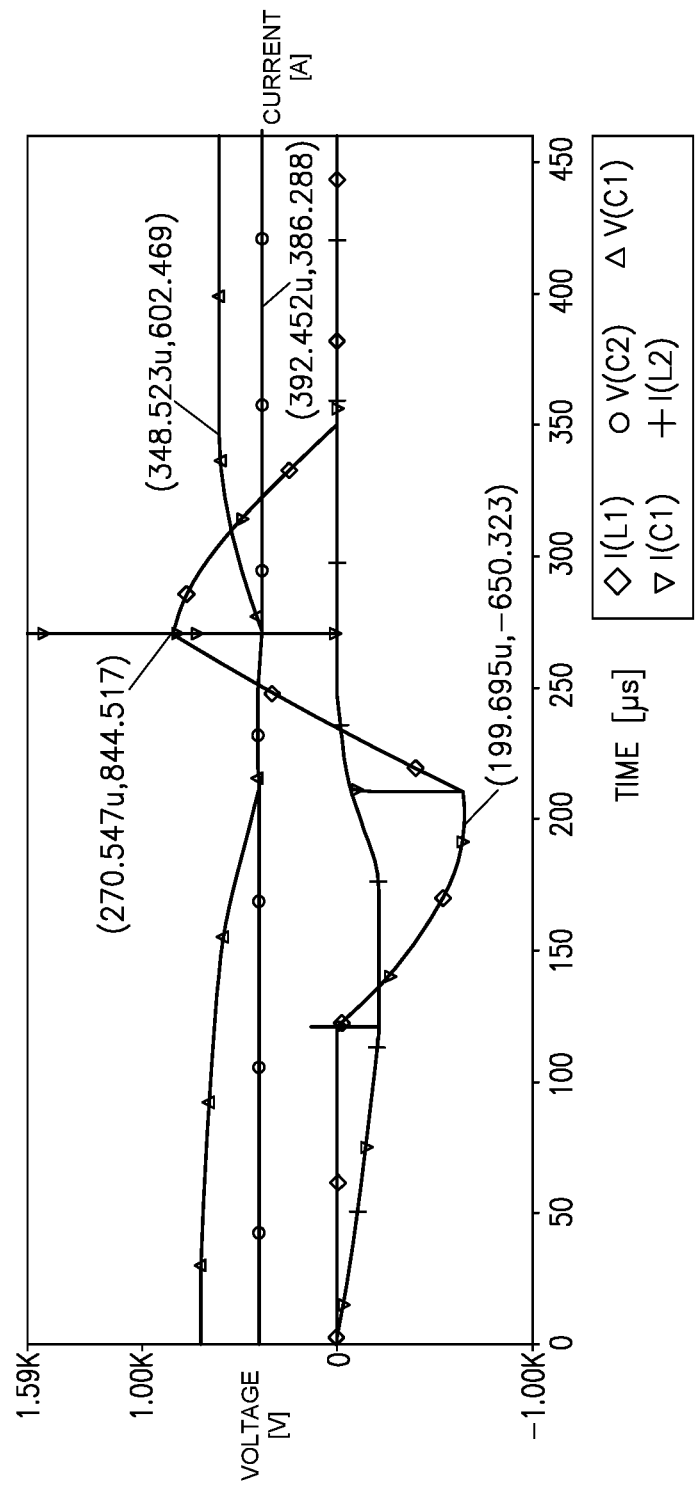
FIG. 26 is a graphical illustration showing pulse shapes which may be produced upon operation of the circuit shown in FIG. 25 in accordance with the parameters of one embodiment of the present invention.

Reference is now made to FIG. 26, which is a graphical illustration showing pulse shapes which may be produced upon operation of the circuit shown in FIG. 25 in accordance with the parameters of Example 17. Initially only switches Z3 and Z5 are opened, hence the current flows initially from capacitor C1 through coil L2. After 120 µs, switch Z5 is closed and Z1 is opened, hence current flows also through L1. At 180 µs switch Z3 is closed, hence the current in L2 starts to decay. Between 210 and 300 µs switch Z1 is closed and Z2 is opened, hence L1 is coupled to C2 instead of C1, and the current in L1 inverts direction, and changes from about −650 A at 210 µs to about 845 A at 300 µs. Note that the relative amplitudes and time interval between the positive and negative peaks may be controlled by the timing of turning on/off of each switch, by the initial voltages on the capacitors, and by the values of capacitances, inductances and resistances in the circuit. At 300 µs, switch Z2 is closed and Z1 is opened, hence L1 is coupled to C1 instead of C2, the current in L1 decays and C1 is recharged.

The voltage on capacitor C1 at the end of a cycle is about 72% ((602V−386V)/300V, see FIG. 26) of its initial value, and in C2 it is about 96% (386V/400V) of its initial value. Since C2 has a larger capacitance, the relative electrical energy loss is smaller.

Example 18

In this non-limiting example, the capacitors have capacitances of C1=180 µF and C2=700 µF, coil L1 has an inductance of 16 µH, coil L2 has an inductance of 150 µH, the resistances in the two coils are R1=R2=0.05 Ohm, and the initial capacitor voltages are V(C1)=300 V and V(C2)=300 V. Hence the voltages on the negative and positive poles of C1 are 300 V and 600 V, respectively. Switches Z1a/b and Z2a/b couple coil L1 with capacitors C1 and C2, respectively. Switches Z3a/b and Z4a/b couple coil L2 with capacitors C1 and C2, respectively. Switches Z5a/b are connected in parallel to coil L1.

Figure 27:
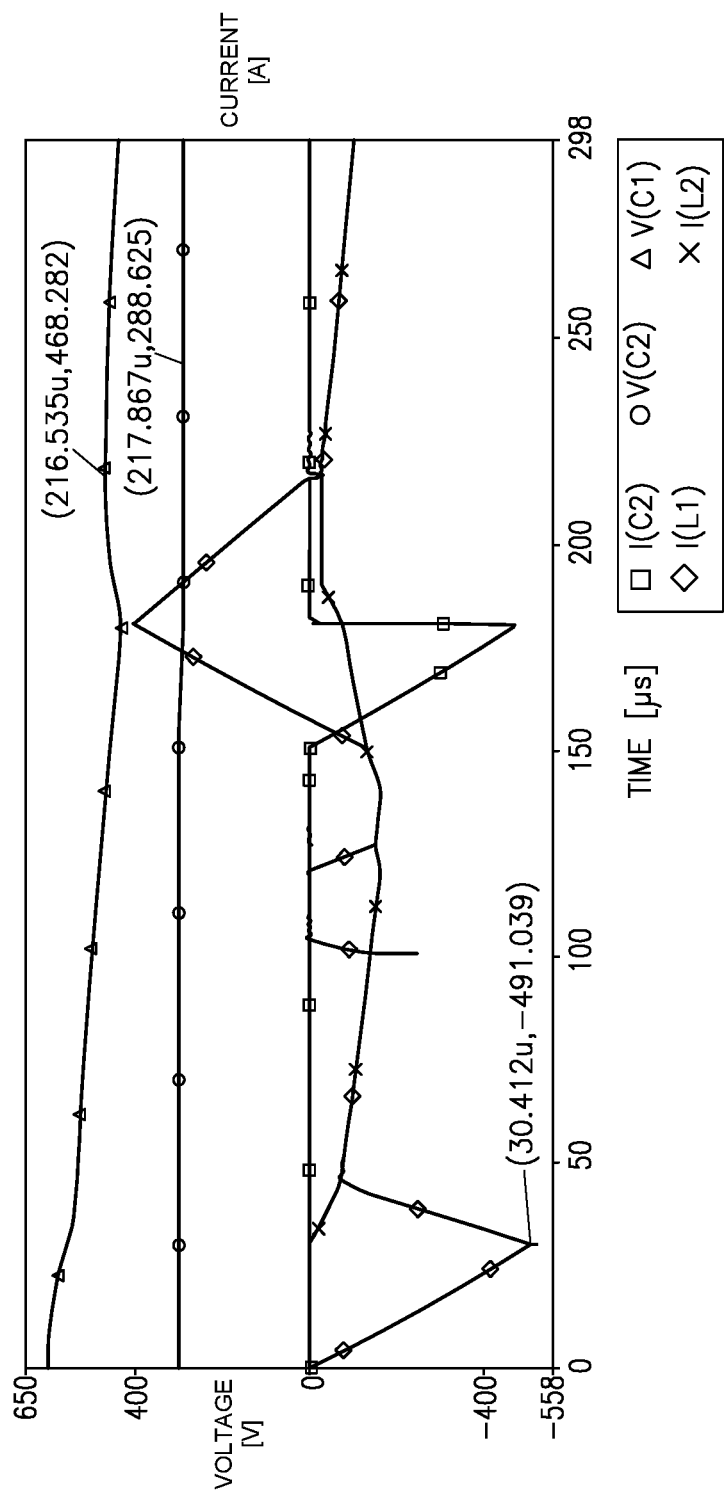
FIG. 27 is a graphical illustration showing pulse shapes which may be produced upon operation of the circuit shown in FIG. 25 in accordance with the parameters of another embodiment of the present invention.

Reference is now made to FIG. 27, which is a graphical illustration showing pulse shapes which may be produced upon operation of the circuit shown in FIG. 25, in accordance with the parameters of Example 18. In this example, initially only switches Z1 and Z6 are opened, hence the current flows initially from capacitor C1 through coil L1.

After 30 µs, when the current through L1 reaches about 490 A, switch Z1 is closed and switch Z3 is opened, hence the current flows through both coil L1 and coil L2 in series. Between 100 µs and 120 µs, switches Z6 and Z1 are closed, and Z5 is opened, hence the current flows through coil L2, and in coil L1 the current decays sharply. At 120 µs, switch Z6 is opened and switch Z5 is closed, hence the current flows through coil L2 and coil L1 in series. At 150 µs, switch Z2 is opened and switch Z3 is closed, hence L1 is coupled to C2 and its current reverses direction. At 180 µs, switch Z2 is closed and switch Z1 is opened, hence L1 is coupled to C1 instead of C2, the current in L1 decays and C1 is recharged. The voltage on capacitor C1 at the end of a cycle is about 60% ((468V−289V)/300V, see FIG. 27) of its initial value, and in C2 it is about 96% (289V/300V) of its initial value.

Again, one can implement each of the above examples with either L1 or L2 or both attached to a body organ, at similar or different locations.

All the non-limiting examples described above, and any other implementation derived from this application, may be generalized to include more than two coils, and/or more than one electrical energy storage device. In certain embodiments, each coil may be coupled to a different electrical energy storage device. In yet other embodiments, some coils may be coupled to a common electrical energy storage device. In yet other embodiments, some coils may be coupled to different electrical energy storage devices during different periods, such as during different phases.

The systems and methods disclosed in this application may be combined using multiple channels, thus potentially providing additional variety of pulse shapes in a body organ. The body organ may be a single body organ or multiple body organs, and the stimulation may be provided over one region or multiple regions of a body organ. For example, different brain regions may be stimulated to produce different physiologic effects in different regions, and/or to increase the specificity of the effect induced in a certain region, such as in deeper neuronal structures. Some examples of physiologic effects may include, but are not limited to, repetitive biphasic pulses, repetitive depolarization of membrane potential, alternating hyperpolarization and depolarization in neuronal structures, hyperpolarization without depolarization, depolarization without hyperpolarization, and others.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A system for producing a physiological effect in a targeted region of an internal body organ using transcranial magnetic stimulation, the system comprising:
  a first electromagnetic coil positionable at a first location, wherein the first location is in close proximity to a body part adjacent the targeted region;

a second electromagnetic coil positioned at a second location, wherein the second location is remote from the first location;

a stimulator for stimulating said first and second electromagnetic coils, the stimulator comprising:

an energy storage device in electrical communication with said first and second electromagnetic coils;

a first externally-controllable fast switch in electrical communication with said first electromagnetic coil and said energy storage device;

a second externally-controllable fast switch in electrical communication with said second electromagnetic coil and said energy storage device; and an external control unit in electrical communication with said first and second externally-controllable fast switches, wherein said control unit is configured to control separate discharge of current into each of said first and second electromagnetic stimulating coils wherein during an initial time period said second externally-controllable fast switch is off and said first externally-controllable fast switch is on, such that current flows from said energy storage device only through said first electromagnetic coil and is isolated from the second location and wherein during the initial time period, current amplitude increases and then decreases until a switching moment, wherein the switching moment occurs within a range of time between the decrease in current amplitude and a time at which a reverse in polarity would occur if the first fast switch is not turned off, wherein at the switching moment the first switch is turned off and the second switch is turned on so that current flows only through the second electromagnetic coil and is isolated from the first location and leads to re-charge of said energy storage device thus resulting in an electric field pulse at the targeted region, the electric field pulse having a symmetric repeatedly monophasic pulse shape generated from the current flow through the first electromagnetic coil.

2. The system of claim 1, further comprising a second energy storage device and a third electromagnetic coil, wherein said second energy storage device is configured to discharge current into said third electromagnetic coil.

3. The system of claim 2, further comprising a third externally-controllable fast switch coupled to said second energy storage device.

4. The system of claim 1, wherein said control unit is further configured to control at least one of the following: an amplitude of initial voltage on said energy storage device, a frequency of discharging of said energy storage device, timing of each pulse or combination of pulses with resolution of microseconds or more, a pulse width of each pulse, relative polarities of current directions in said first and second electromagnetic coils at each period of operation, direction of current flow in said first and second electromagnetic coils at each period of operation, and numbers of each type of pulse.

5. The system of claim 1, wherein the targeted region is a neuronal tissue in a brain, spinal cord or in a peripheral nerve.

6. The system of claim 1, wherein said first electromagnetic coil has a different inductance than said second electromagnetic coil.

7. The system of claim 1, wherein said first electromagnetic coil is connected in series to said second electromagnetic coil.

8. The system of claim 1, wherein when current flow from said energy storage device through said first electromagnetic coil is isolated from the second location, simultaneous current flow is provided from the energy storage device through the second electromagnetic coil.

9. A system for producing a physiological effect in a targeted region of an internal body organ using transcranial magnetic stimulation, the system comprising:

a first electromagnetic coil positionable at a first location, wherein the first location is in close proximity to a body part adjacent the targeted region;

a second electromagnetic coil positioned at a second location, wherein the second location is remote from the first location;

a stimulator for stimulating said first and second electromagnetic coils, the stimulator comprising:

an energy storage device in electrical communication with said first and second electromagnetic coils;

a first externally-controllable fast switch in electrical communication with said first electromagnetic coil and said energy storage device;

a second externally-controllable fast switch in electrical communication with said second electromagnetic coil and said energy storage device; and an external control unit in electrical communication with said first and second externally-controllable fast switches, wherein said control unit is configured to control separate discharge of current into each of said first and second electromagnetic stimulating coils wherein during an initial time period said first externally-controllable fast switch is off and said second externally-controllable fast switch is on, such that current flows from said energy storage device only through said second electromagnetic coil and is isolated from the first location and wherein during the initial time period, current amplitude increases and then decreases until a switching moment, wherein the switching moment occurs within a range of time between the decrease in current amplitude and a time at which a reverse in polarity would occur if the second fast switch is not turned off, wherein at the switching moment the second switch is turned off and the first switch is turned on so that current flows only through the first electromagnetic coil and is isolated from the second location and leads to re-charge of said energy storage device thus resulting in an electric field pulse at the targeted region, the electric field pulse having a symmetric repeatedly monophasic pulse shape generated from the current flow through the first electromagnetic coil.

10. The system of claim 9, further comprising a second energy storage device and a third electromagnetic coil, wherein said second energy storage device is configured to discharge current into said third electromagnetic coil.

11. The system of claim 10, further comprising a third externally-controllable fast switch coupled to said second energy storage device.

12. The system of claim 9, wherein said control unit is further configured to control at least one of the following: an amplitude of initial voltage on said energy storage device, a frequency of discharging of said energy storage device, timing of each pulse or combination of pulses with resolution of microseconds or more, a pulse width of each pulse, relative polarities of current directions in said first and second electromagnetic coils at each period of operation, direction of current flow in said first and second electromagnetic coils at each period of operation, and numbers of each type of pulse.

13. The system of claim 9, wherein the targeted region is a neuronal tissue in a brain, spinal cord or in a peripheral nerve.

14. The system of claim 9, wherein said first electromagnetic coil has a different inductance than said second electromagnetic coil.

15. The system of claim 9, wherein said first electromagnetic coil is connected in series to said second electromagnetic coil.

16. The system of claim 9, wherein when current flow from said energy storage device through said first electromagnetic coil is isolated from the second location, simultaneous current flow is provided from the energy storage device through the second electromagnetic coil.

* * * * *